US012793817B2

(12) United States Patent
Williams et al.

(10) Patent No.: US 12,793,817 B2
(45) Date of Patent: Nov. 10, 2026

(54) MULTI-TENANT CLINICAL RESEARCH PLATFORM FOR REMOTE MANAGEMENT OF CLINICAL RESEARCH SITES FOR PATIENTS

(71) Applicant: IQVIA, Inc., Parsippany, NJ (US)

(72) Inventors: Brian Wilson Williams, Apex, NC (US); Jonathan Anthony Walter, Raleigh, NC (US); Akshara T Gopalakrishna, Bangalore (IN); Sumanta Sharma, Holly Springs, NC (US)

(73) Assignee: IQVIA Inc., Parsippany, NJ (US)

( * ) Notice: Subject to any disclaimer, the term of this patent is extended or adjusted under 35 U.S.C. 154(b) by 30 days.

(21) Appl. No.: 19/064,158

(22) Filed: Feb. 26, 2025

(65) Prior Publication Data

US 2025/0273308 A1 Aug. 28, 2025

Related U.S. Application Data

(60) Provisional application No. 63/557,982, filed on Feb. 26, 2024.

(51) Int. Cl.
*G16H 10/20* (2018.01)
*G16H 10/60* (2018.01)

(52) U.S. Cl.
CPC ............. *G16H 10/20* (2018.01); *G16H 10/60* (2018.01)

(58) Field of Classification Search
CPC ............................... G16H 10/20; G16H 10/60
See application file for complete search history.

(56) References Cited

U.S. PATENT DOCUMENTS 7,676,386 B2 3/2010 Stephenson
7,689,439 B2 3/2010 Parker
(Continued)

FOREIGN PATENT DOCUMENTS

CN 114913943 A * 8/2022 ............. G16H 10/20

OTHER PUBLICATIONS

Wang et al.; Clinical Source Data Production and Quality Control in Real world Studies: Method Design for the eSource Record Tool (the ESR Study); JMIR; 31 pages; Sep. 16, 2022 (Year: 2022).*
(Continued)

*Primary Examiner* — Richard G Keehn
(74) *Attorney, Agent, or Firm* — ALG Intellectual Property, LLC

(57) ABSTRACT

Systems and methods provide efficient access to electronic data capture (EDC) and electronic medical record (EMR) data for monitoring clinical research. A multi-tenant clinical research platform is configured to support remote management of clinical research sites based on EDC and EMR data. The platform is configured to access EDC data from an EDC data store, access related EMR data from an EMR data store that is separate from the EDC data store, and use mappings between the EDC data and the EMR data to contextually integrate the EMR data into a clinical research review workflow provided by the platform. In some embodiments, the platform is configured to prevent persistence of the EDC data and/or EMR data within the platform. The platform provides remote, on-demand controlled access to the EDC data and the EMR data to facilitate offsite reviews of clinical research sites based on EDC and EMR data.

20 Claims, 20 Drawing Sheets

(56) References Cited

U.S. PATENT DOCUMENTS

| | | | | |
|---|---|---|---|---|
| 8,155,980 | B2 | 4/2012 | Parker | |
| 10,366,781 | B1 | 7/2019 | Menon et al. | |
| 10,424,400 | B2 | 9/2019 | Menon et al. | |
| 11,106,569 | B1 | 8/2021 | Chapagain et al. | |
| 11,309,065 | B2 | 4/2022 | Hassett | |
| 11,526,953 | B2 | 12/2022 | Bonageri et al. | |
| 12,592,319 | B1 * | 3/2026 | Shorter | G16H 10/20 |
| 12,640,240 | B2 | 5/2026 | Adhikari et al. | |
| 2002/0010679 | A1 * | 1/2002 | Felsher | G16H 10/60<br>705/51 |
| 2010/0241595 | A1 * | 9/2010 | Felsher | G16H 10/60<br>707/E17.014 |
| 2011/0301982 | A1 * | 12/2011 | Green, Jr. | G06Q 10/10<br>705/3 |
| 2012/0101837 | A1 | 4/2012 | McCorkle et al. | |
| 2012/0101838 | A1 | 4/2012 | Lingard et al. | |
| 2013/0238642 | A1 | 9/2013 | Clayton et al. | |
| 2013/0311196 | A1 * | 11/2013 | Fay | G16H 10/20<br>705/2 |
| 2014/0222463 | A1 * | 8/2014 | Guthrie, Jr. | G16H 10/20<br>705/3 |
| 2015/0081336 | A1 | 3/2015 | Hill et al. | |
| 2015/0127372 | A1 | 5/2015 | Berry | |
| 2015/0186618 | A1 * | 7/2015 | Poorvin | G16H 10/20<br>705/3 |
| 2019/0180862 | A1 * | 6/2019 | Wisser | G16H 10/60 |
| 2020/0294642 | A1 * | 9/2020 | Bostic | G16H 10/60 |
| 2021/0090745 | A1 | 3/2021 | Leavitt et al. | |
| 2022/0359048 | A1 | 11/2022 | Patil et al. | |
| 2022/0375550 | A1 * | 11/2022 | Shi | G16H 10/20 |
| 2023/0127903 | A1 | 4/2023 | Lin et al. | |
| 2023/0317261 | A1 | 10/2023 | Vanggaard et al. | |
| 2023/0335232 | A1 | 10/2023 | Jin et al. | |
| 2024/0006041 | A1 | 1/2024 | Walter et al. | |
| 2024/0020547 | A1 | 1/2024 | Renstroem et al. | |
| 2024/0047044 | A1 * | 2/2024 | Wisser | G16H 10/60 |
| 2024/0054419 | A1 * | 2/2024 | Renstroem | G06Q 10/0635 |
| 2024/0127914 | A1 * | 4/2024 | Kroeker | G16H 10/60 |
| 2025/0087372 | A1 | 3/2025 | Bonageri et al. | |
| 2025/0201422 | A1 | 6/2025 | Leavitt et al. | |

OTHER PUBLICATIONS

Wang et al.; Electronic Source Data Transcription for Electronic Case Report Forms in China: Validation of the Electronic Source Record Tool in a Real-world Ophthalmology Study; JMIR; 13 pages; Dec. 16, 2022 (Year: 2022).*

* cited by examiner

MULTI-TENANT CLINICAL RESEARCH PLATFORM FOR REMOTE MANAGEMENT OF CLINICAL RESEARCH SITES FOR PATIENTS

RELATED APPLICATIONS

The present application claims priority to U.S. Provisional Patent Application No. 63/557,982, filed Feb. 26, 2024, the content of which is hereby incorporated by reference in its entirety.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Various illustrative embodiments are described herein with reference to the accompanying drawings. It will, however, be evident that various modifications and changes may be made thereto, and additional embodiments may be implemented, without departing from the scope of the invention as set forth in the claims. For example, certain features of one embodiment described herein may be combined with or substituted for features of another embodiment described herein. The description and drawings are accordingly to be regarded in an illustrative rather than a restrictive sense.

Figure 1A:
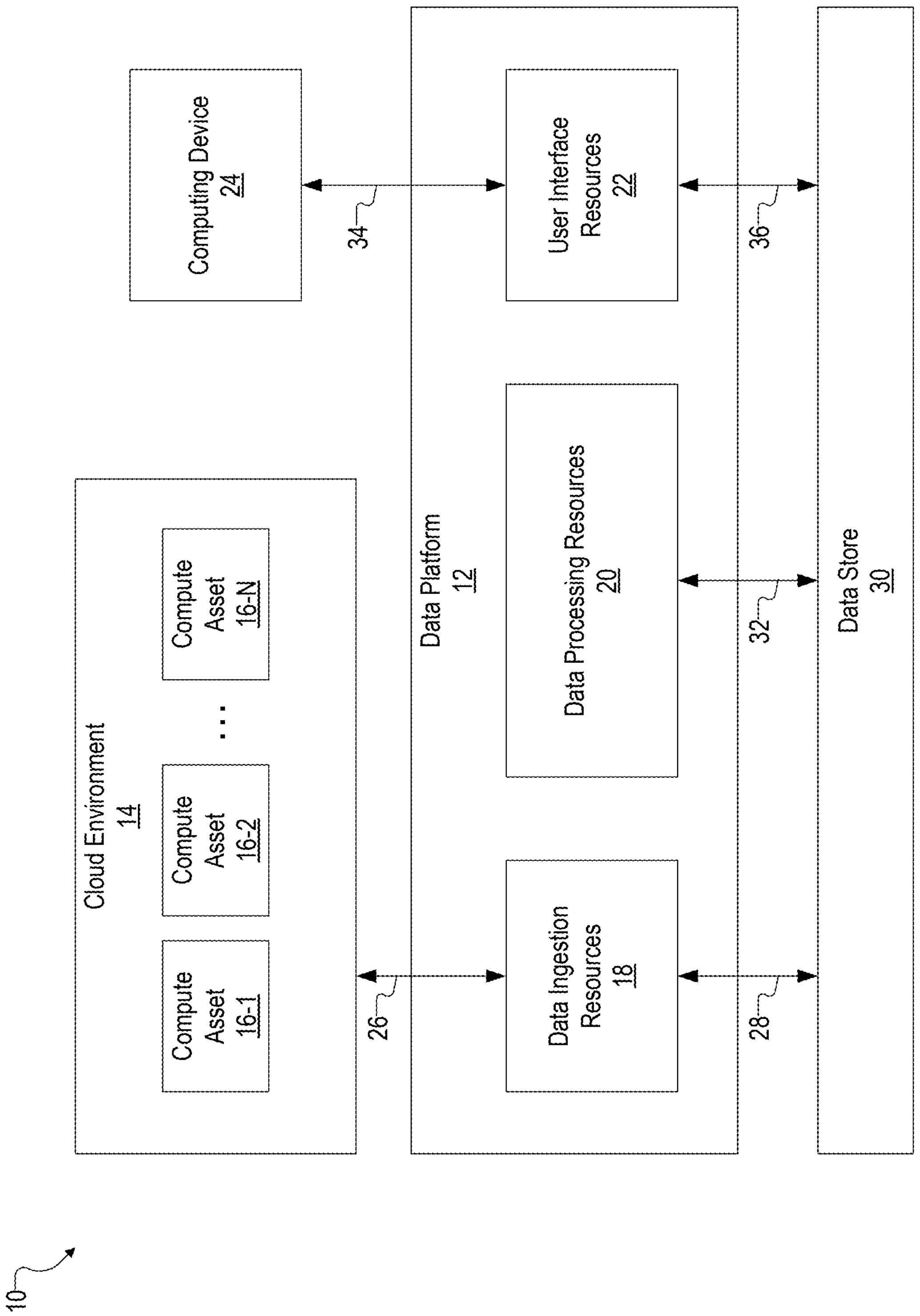
FIG. 1A shows an illustrative configuration in which a data platform is configured to perform various operations with respect to a cloud environment that includes a plurality of compute assets.

FIG. 1A shows an illustrative configuration 10 in which a data platform 12 is configured to perform various operations with respect to a cloud environment 14 that includes a plurality of compute assets 16-1 through 16-N (collectively "compute assets 16"). For example, data platform 12 may include data ingestion resources 18 configured to ingest data from cloud environment 14 into data platform 12, data processing resources 20 configured to perform data processing operations with respect to the data, and user interface resources 22 configured to provide one or more external users and/or compute resources (e.g., computing device 24) with access to an output of data processing resources 20. Each of these resources are described in detail herein.

Cloud environment 14 may include any suitable network-based computing environment as may serve a particular application. For example, cloud environment 14 may be implemented by one or more compute resources provided and/or otherwise managed by one or more cloud service providers, such as Amazon Web Services (AWS), Google Cloud Platform (GCP), Microsoft Azure, and/or any other cloud service provider configured to provide public and/or private access to network-based compute resources.

Compute assets 16 may include, but are not limited to, containers (e.g., container images, deployed and executing container instances, etc.), virtual machines, workloads, applications, processes, physical machines, compute nodes, clusters of compute nodes, software runtime environments (e.g., container runtime environments), and/or any other virtual and/or physical compute resource that may reside in and/or be executed by one or more computer resources in cloud environment 14. In some examples, one or more compute assets 16 may reside in one or more datacenters.

A compute asset 16 may be associated with (e.g., owned, deployed, or managed by) a particular entity, such as a customer or client of cloud environment 14 and/or data platform 12. Accordingly, for purposes of the discussion herein, cloud environment 14 may be used by one or more entities.

Data platform 12 may be configured to perform one or more data monitoring and/or remediation services, compliance monitoring services, anomaly detection services, DevOps services, compute asset management services, and/or any other type of data analytics service as may serve a particular implementation. Data platform 12 may be managed or otherwise associated with any suitable data platform provider, such as a provider of any of the data analytics services described herein. The various resources included in data platform 12 may reside in the cloud and/or be located on-premises and be implemented by any suitable combination of physical and/or virtual compute resources, such as one or more computing devices, microservices, applications, etc.

Data ingestion resources 18 may be configured to ingest data from cloud environment 14 into data platform 12. This may be performed in various ways, some of which are described in detail herein. For example, as illustrated by arrow 26, data ingestion resources 18 may be configured to receive the data from one or more agents deployed within cloud environment 14, utilize an event streaming platform (e.g., Kafka) to obtain the data, and/or pull data (e.g., configuration data) from cloud environment 14. In some examples, data ingestion resources 18 may obtain the data using one or more agentless configurations.

The data ingested by data ingestion resources 18 from cloud environment 14 may include any type of data as may serve a particular implementation. For example, the data may include data representative of configuration information associated with compute assets 16, information about one or more processes running on compute assets 16, network activity information, information about events (creation events, modification events, communication events, user-initiated events, etc.) that occur with respect to compute assets 16, etc. In some examples, the data may or may not include actual customer data processed or otherwise generated by compute assets 16.

As illustrated by arrow 28, data ingestion resources 18 may be configured to load the data ingested from cloud environment 14 into a data store 30. Data store 30 is illustrated in FIG. 1A as being separate from and communicatively coupled to data platform 12. However, in some alternative embodiments, data store 30 is included within data platform 12.

Data store 30 may be implemented by any suitable data warehouse, data lake, data mart, and/or other type of database structure as may serve a particular implementation. Such data stores may be proprietary or may be embodied as vendor provided products or services such as, for example, Snowflake, Google BigQuery, Druid, Amazon Redshift, IBM db2, Dremio, Databricks Lakehouse Platform, Cloudera, Azure Synapse Analytics, and others.

Although the examples described herein largely relate to embodiments where data is collected from agents and ultimately stored in a data store such as those provided by Snowflake, in other embodiments data that is collected from agents and other sources may be stored in different ways. For example, data that is collected from agents and other sources may be stored in a data warehouse, data lake, data mart, and/or any other data store.

A data warehouse may be embodied as an analytic database (e.g., a relational database) that is created from two or more data sources. Such a data warehouse may be leveraged to store historical data, often on the scale of petabytes. Data warehouses may have compute and memory resources for running complicated queries and generating reports. Data warehouses may be the data sources for business intelligence ('BI') systems, machine learning applications, data source monitoring/management applications, and/or other applications. By leveraging a data warehouse, data that has been copied into the data warehouse may be indexed for good analytic query performance, without affecting the write performance of a database (e.g., an Online Transaction Processing ('OLTP') database). Data warehouses also enable joining data from multiple sources for analysis. For example, a sales OLTP application probably has no need to know about the weather at various sales locations, but sales predictions could take advantage of that data. By adding historical weather data to a data warehouse, it would be possible to factor it into models of historical sales data.

Data lakes, which store files of data in their native format, may be considered as "schema on read" resources. As such, any application that reads data from the lake may impose its own types and relationships on the data. Data warehouses, on the other hand, are "schema on write," meaning that data types, indexes, and relationships are imposed on the data as it is stored in an enterprise data warehouse (EDW). "Schema on read" resources may be beneficial for data that may be used in several contexts and poses little risk of losing data. "Schema on write" resources may be beneficial for data that has a specific purpose, and good for data that must relate properly to data from other sources. Such data stores may include data that is encrypted using homomorphic encryption, data encrypted using privacy-preserving encryption, smart contracts, non-fungible tokens, decentralized finance, and other techniques.

Data marts may contain data oriented towards a specific business line whereas data warehouses contain enterprise-wide data. Data marts may be dependent on a data warehouse, independent of the data warehouse (e.g., drawn from an operational database or external source), or a hybrid of the two. In embodiments described herein, different types of data stores (including combinations thereof) may be leveraged.

Data processing resources 20 may be configured to perform various data processing operations with respect to data ingested by data ingestion resources 18, including data ingested and stored in data store 30. For example, data processing resources 20 may be configured to perform one or more data monitoring and/or remediation operations, compliance monitoring operations, anomaly detection operations, DevOps operations, compute asset management operations, and/or any other type of data analytics operation as may serve a particular implementation. Various examples of operations performed by data processing resources 20 are described herein.

As illustrated by arrow 32, data processing resources 20 may be configured to access data in data store 30 to perform the various operations described herein. In some examples, this may include performing one or more queries with respect to the data stored in data store 30. Such queries may be generated using any suitable query language.

In some examples, the queries provided by data processing resources 20 may be configured to direct data store 30 to perform one or more data analytics operations with respect to the data stored within data store 30. These data analytics operations may be with respect to data specific to a particular entity (e.g., data residing in one or more silos within data store 30 that are associated with a particular customer) and/or data associated with multiple entities. For example, data processing resources 20 may be configured to analyze data associated with a first entity and use the results of the analysis to perform one or more operations with respect to a second entity.

One or more operations performed by data processing resources 20 may be performed periodically according to a predetermined schedule. For example, one or more operations may be performed by data processing resources 20 every hour or any other suitable time interval.

Additionally or alternatively, one or more operations performed by data processing resources 20 may be performed in substantially real-time (or near real-time) as data is ingested into data platform 12. In this manner, the results of such operations (e.g., one or more detected anomalies in the data) may be provided to one or more external entities (e.g., computing device 24 and/or one or more users) in substantially real-time and/or in near real-time.

User interface resources 22 may be configured to perform one or more user interface operations, examples of which are described herein. For example, user interface resources 22 may be configured to present one or more results of the data processing performed by data processing resources 20 to one or more external entities (e.g., computing device 24 and/or one or more users), as illustrated by arrow 34. As illustrated by arrow 36, user interface resources 22 may access data in data store 30 to perform the one or more user interface operations.

Figure 1B:
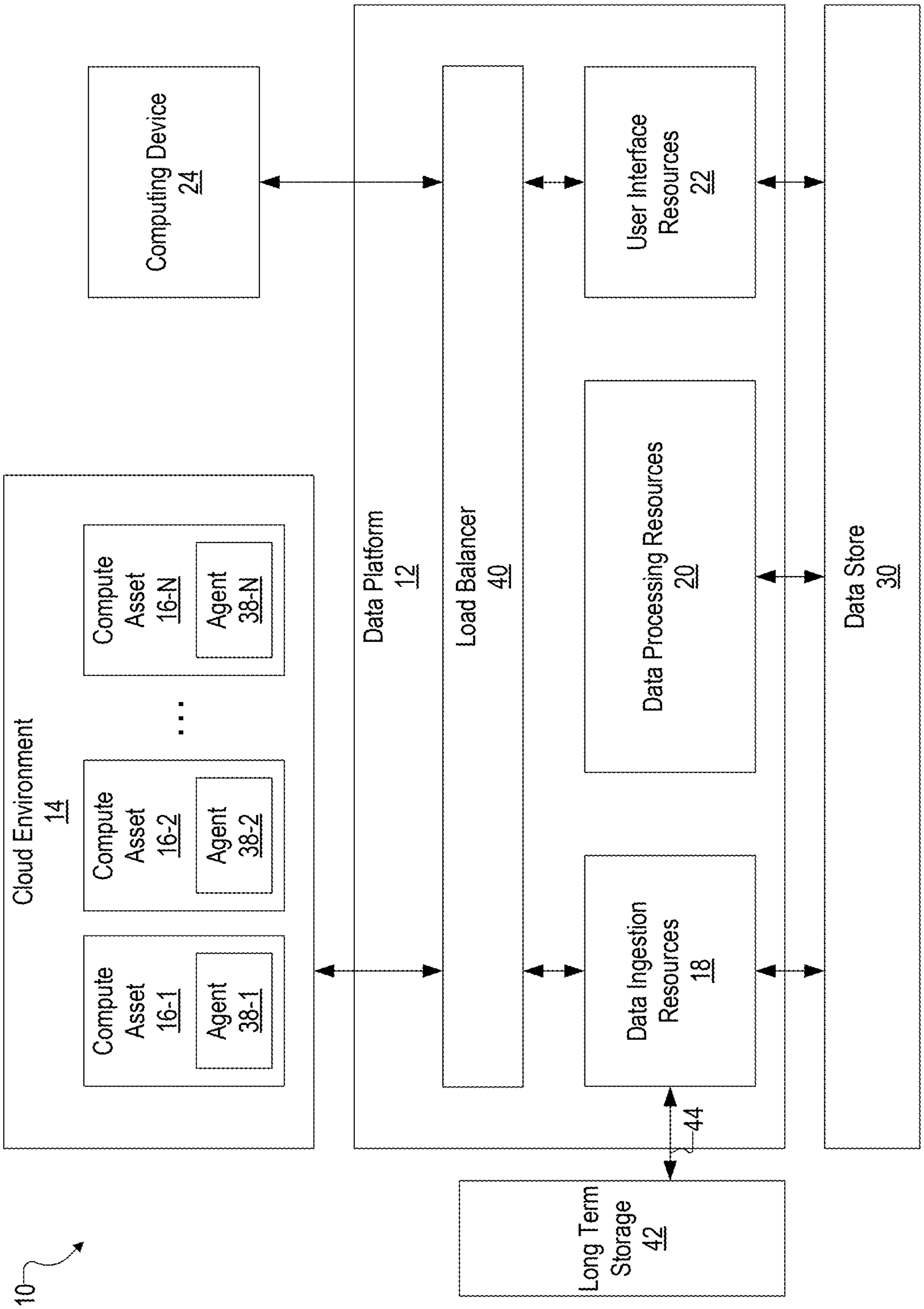
FIG. 1B shows an illustrative implementation of the configuration of FIG. 1A.

FIG. 1B illustrates an implementation of configuration 10 in which an agent 38 (e.g., agent 38-1 through agent 38-N) is installed on each of compute assets 16. As used herein, an agent may include a self-contained binary and/or other type of code or application that can be run on any appropriate platforms, including within containers and/or other virtual compute assets. Agents 38 may monitor the nodes on which they execute for a variety of different activities, including but not limited to, connection, process, user, machine, and file activities. In some examples, agents 38 can be executed in user space, and can use a variety of kernel modules (e.g., auditd, iptables, netfilter, pcap, etc.) to collect data. Agents can be implemented in any appropriate programming language, such as C or Golang, using applicable kernel APIs.

Agents 38 may be deployed in any suitable manner. For example, an agent 38 may be deployed as a containerized application or as part of a containerized application. As described herein, agents 38 may selectively report information to data platform 12 in varying amounts of detail and/or with variable frequency.

Also shown in FIG. 1B is a load balancer 40 configured to perform one or more load balancing operations with respect to data ingestion operations performed by data ingestion resources 18 and/or user interface operations performed by user interface resources 22. Load balancer 40 is shown to be included in data platform 12. However, load balancer 40 may alternatively be located external to data platform 12. Load balancer 40 may be implemented by any suitable microservice, application, and/or other computing resources. In some alternative examples, data platform 12 may not utilize a load balancer such as load balancer 40.

Also shown in FIG. 1B is long term storage 42 with which data ingestion resources 18 may interface, as illustrated by arrow 44. Long term storage 42 may be implemented by any suitable type of storage resources, such as cloud-based storage (e.g., AWS S3, etc.) and/or on-premises storage and may be used by data ingestion resources 18 as part of the data ingestion process. Examples of this are described herein. In some examples, data platform 12 may not utilize long term storage 42.

The embodiments described herein can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the principles described herein. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 1C:
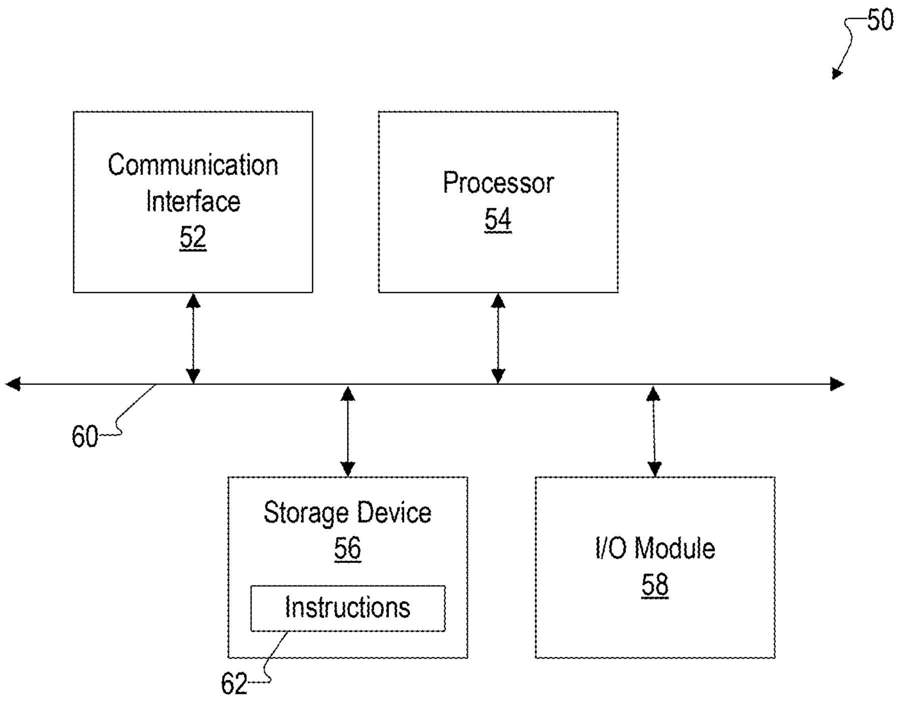
FIG. 1C illustrates an example computing device.

FIG. 1C illustrates an example computing device 50 that may be specifically configured to perform one or more of the processes described herein. Any of the systems, microservices, computing devices, and/or other components described herein may be implemented by computing device 50.

As shown in FIG. 1C, computing device 50 may include a communication interface 52, a processor 54, a storage device 56, and an input/output ("I/O") module 58 communicatively connected one to another via a communication infrastructure 60. While an exemplary computing device 50 is shown in FIG. 1C, the components illustrated in FIG. 1C are not intended to be limiting. Additional or alternative components may be used in other embodiments. Components of computing device 50 shown in FIG. 1C will now be described in additional detail.

Communication interface 52 may be configured to communicate with one or more computing devices. Examples of communication interface 52 include, without limitation, a wired network interface (such as a network interface card), a wireless network interface (such as a wireless network interface card), a modem, an audio/video connection, and any other suitable interface.

Processor 54 generally represents any type or form of processing unit capable of processing data and/or interpreting, executing, and/or directing execution of one or more of the instructions, processes, and/or operations described herein. Processor 54 may perform operations by executing computer-executable instructions 62 (e.g., an application, software, code, and/or other executable data instance such as a computer program product) stored in storage device 56.

Storage device 56 may include one or more data storage media, devices, or configurations and may employ any type, form, and combination of data storage media and/or device. For example, storage device 56 may include, but is not limited to, any combination of the non-volatile media and/or volatile media described herein. Electronic data, including data described herein, may be temporarily and/or permanently stored in storage device 56. For example, data representative of computer-executable instructions 62 configured to direct processor 54 to perform any of the operations described herein may be stored within storage device 56. In some examples, data may be arranged in one or more databases residing within storage device 56.

I/O module 58 may include one or more I/O modules configured to receive user input and provide user output. I/O module 58 may include any hardware, firmware, software, or combination thereof supportive of input and output capabilities. For example, I/O module 58 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 58 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 58 is configured to provide graphical data to a display for presentation to a user. The graphical data may be representative of one or more graphical user interfaces and/or any other graphical content as may serve a particular implementation.

Figure 1D:
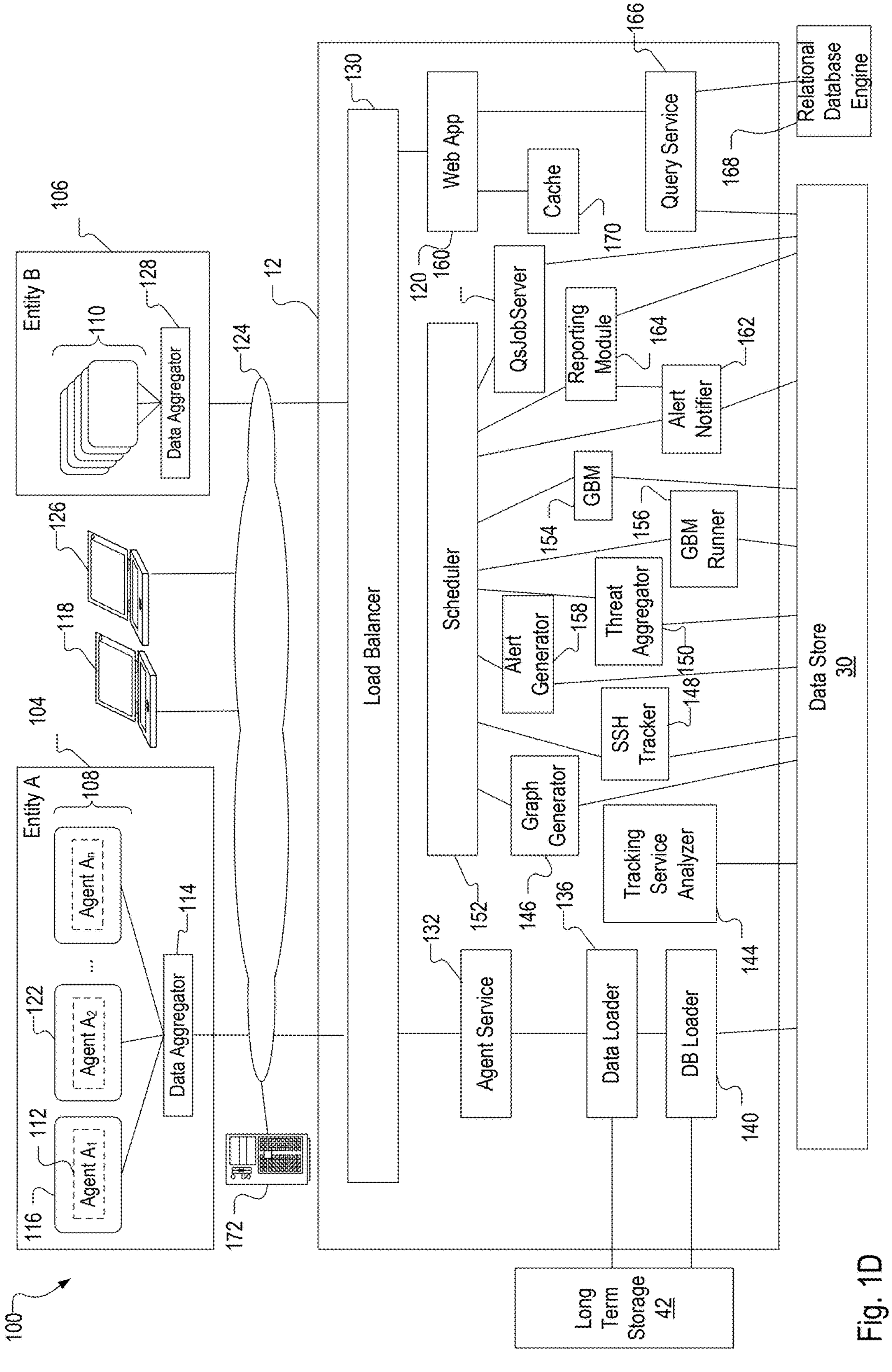
FIG. 1D illustrates an example of an environment in which activities that occur within datacenters are modeled.

FIG. 1D illustrates an example implementation 100 of configuration 10. As such, one or more components shown in FIG. 1D may implement one or more components shown in FIG. 1A and/or FIG. 1B. In particular, implementation 100 illustrates an environment in which activities that occur within datacenters are modeled using data platform 12. Using techniques described herein, a baseline of datacenter activity can be modeled, and deviations from that baseline can be identified as anomalous. Anomaly detection can be beneficial in a data observation context, a compliance context, an asset management context, a DevOps context, and/or any other data analytics context as may serve a particular implementation.

Two example datacenters (104 and 106) are shown in FIG. 1D, and are associated with (e.g., belong to) entities named entity A and entity B, respectively. A datacenter may include dedicated equipment (e.g., owned and operated by entity A, or owned/leased by entity A and operated exclusively on entity A's behalf by a third party). A datacenter can also include cloud-based resources, such as infrastructure as a service (IaaS), platform as a service (PaaS), and/or software as a service (SaaS) elements. The techniques described herein can be used in conjunction with multiple types of datacenters, including ones wholly using dedicated equipment, ones that are entirely cloud-based, and ones that use a mixture of both dedicated equipment and cloud-based resources.

Both datacenter 104 and datacenter 106 include a plurality of nodes, depicted collectively as set of nodes 108 and set of nodes 110, respectively, in FIG. 1D. These nodes may implement compute assets 16. Installed on each of the nodes are in-server/in-virtual-machine (VM)/embedded-in-IoT device agents (e.g., agent 112), which are configured to collect data and report it to data platform 12 for analysis. As described herein, agents may be small, self-contained binaries that can be run on any appropriate platforms, including virtualized ones (and, as applicable, within containers). Agents may monitor the nodes on which they execute for a variety of different activities, including: connection, process, user, machine, and file activities. Agents can be executed in user space, and can use a variety of kernel modules (e.g., auditd, iptables, netfilter, pcap, etc.) to collect data. Agents can be implemented in any appropriate programming language, such as C or Golang, using applicable kernel APIs.

As described herein, agents can selectively report information to data platform 12 in varying amounts of detail and/or with variable frequency. As is also described herein, the data collected by agents may be used by data platform 12 to create various types of graphs (e.g., knowledge graphs, graphs of logical entities connected by behaviors, etc.). In some embodiments, agents report information directly to data platform 12. In other embodiments, at least some agents provide information to a data aggregator, such as data aggregator 114, which in turn provides information to data platform 12.

The functionality of a data aggregator can be implemented as a separate binary or other application (distinct from an agent binary), and can also be implemented by having an agent execute in an "aggregator mode" in which the designated aggregator node acts as a Layer 7 proxy for other agents that do not have access to data platform 12. Further, a chain of multiple aggregators can be used, if applicable (e.g., with agent 112 providing data to data aggregator 114, which in turn provides data to another aggregator (not pictured) which provides data to data platform 12). An example way to implement an aggregator is through a program written in an appropriate language, such as C or Golang.

Use of an aggregator can be beneficial in sensitive environments (e.g., involving financial or medical transactions or events) where various nodes are subject to regulatory or other architectural requirements (e.g., prohibiting a given node from communicating with systems outside of datacenter 104). Use of an aggregator can also help to minimize data exposure more generally. As one example, by limiting communications with data platform 12 to data aggregator 114, individual nodes in nodes 108 need not make external network connections (e.g., via Internet 124), which can potentially expose them to compromise (e.g., by other external devices, such as device 118, operated by a criminal). Similarly, data platform 12 can provide updates, configuration information, etc., to data aggregator 114 (which in turn distributes them to nodes 108), rather than requiring nodes 108 to allow incoming connections from data platform 12 directly.

Another benefit of an aggregator model is that network congestion can be reduced (e.g., with a single connection being made at any given time between data aggregator 114 and data platform 12, rather than potentially many different connections being open between various of nodes 108 and data platform 12). Similarly, network consumption can also be reduced (e.g., with the aggregator applying compression techniques/bundling data received from multiple agents).

One example way that an agent (e.g., agent 112, installed on node 116) can provide information to data aggregator 114 is via a REST API, formatted using data serialization protocols such as Apache Avro. One example type of information sent by agent 112 to data aggregator 114 is status information. Status information may be sent by an agent periodically (e.g., once an hour or once any other predetermined amount of time). Alternatively, status information may be sent continuously or in response to occurrence of one or more events. The status information may include, but is not limited to, a. an amount of event backlog (in bytes) that has not yet been transmitted, b. configuration information, c. any data loss period for which data was dropped, d. a cumulative count of errors encountered since the agent started, e. version information for the agent binary, and/or f cumulative statistics on data collection (e.g., number of network packets processed, new processes seen, etc.).

A second example type of information that may be sent by agent 112 to data aggregator 114 is event data (described in more detail herein), which may include a UTC timestamp for each event. As applicable, the agent can control the amount of data that it sends to the data aggregator in each call (e.g., a maximum of 10 MB) by adjusting the amount of data sent to manage the conflicting goals of transmitting data as soon as possible and maximizing throughput. Data can also be compressed or uncompressed by the agent (as applicable) prior to sending the data.

Each data aggregator may run within a particular customer environment. A data aggregator (e.g., data aggregator 114) may facilitate data routing from many different agents (e.g., agents executing on nodes 108) to data platform 12. In various embodiments, data aggregator 114 may implement a SOCKS 5 caching proxy through which agents can connect to data platform 12. As applicable, data aggregator 114 can encrypt (or otherwise obfuscate) sensitive information prior to transmitting it to data platform 12, and can also distribute key material to agents which can encrypt the information (as applicable). Data aggregator 114 may include a local storage, to which agents can upload data (e.g., pcap packets). The storage may have a key-value interface. The local storage can also be omitted, and agents configured to upload data to a cloud storage or other storage area, as applicable. Data aggregator 114 can, in some embodiments, also cache locally and distribute software upgrades, patches, or configuration information (e.g., as received from data platform 12).

Various examples associated with agent data collection and reporting will now be described.

In the following example, suppose that a user (e.g., a network administrator) at entity A (hereinafter "user A") has decided to begin using the services of data platform 12. In some embodiments, user A may access a web frontend (e.g., web app 120) using a computer 126 and enrolls (on behalf of entity A) an account with data platform 12. After enrollment is complete, user A may be presented with a set of installers, pre-built and customized for the environment of entity A, that user A can download from data platform 12 and deploy on nodes 108. Examples of such installers include, but are not limited to, a Windows executable file, an iOS app, a Linux package (e.g., .deb or .rpm), a binary, or a container (e.g., a Docker container). When a user (e.g., a network administrator) at entity B (hereinafter "user B") also signs up for the services of data platform 12, user B may be similarly presented with a set of installers that are pre-built and customized for the environment of entity B.

User A deploys an appropriate installer on each of nodes 108 (e.g., with a Windows executable file deployed on a Windows-based platform or a Linux package deployed on a Linux platform, as applicable). As applicable, the agent can be deployed in a container. Agent deployment can also be performed using one or more appropriate automation tools, such as Chef, Puppet, Salt, and Ansible. Deployment can also be performed using managed/hosted container management/orchestration frameworks such as Kubernetes, Mesos, and/or Docker Swarm.

In various embodiments, the agent may be installed in the user space (i.e., is not a kernel module), and the same binary is executed on each node of the same type (e.g., all Windows-based platforms have the same Windows-based binary installed on them). An illustrative function of an agent, such as agent 112, is to collect data (e.g., associated with node 116) and report it (e.g., to data aggregator 114). Other tasks that can be performed by agents include data configuration and upgrading.

One approach to collecting data as described herein is to collect virtually all information available about a node (and, e.g., the processes running on it). Alternatively, the agent may monitor for network connections, and then begin collecting information about processes associated with the network connections, using the presence of a network packet associated with a process as a trigger for collecting additional information about the process. As an example, if a user of node 116 executes an application, such as a calculator application, which does not typically interact with the network, no information about use of that application may be collected by agent 112 and/or sent to data aggregator 114. If, however, the user of node 116 executes an ssh command (e.g., to ssh from node 116 to node 122), agent 112 may collect information about the process and provide associated information to data aggregator 114. In various embodiments, the agent may always collect/report information about certain events, such as privilege escalation, irrespective of whether the event is associated with network activity.

In some examples, data aggregator 114 may be configured to provide information (e.g., collected from nodes 108 by agents) to data platform 12. Data aggregator 128 may be similarly configured to provide information to data platform 12. As shown in FIG. 1D, both aggregator 114 and aggregator 128 may connect to a load balancer 130, which accepts connections from aggregators (and/or as applicable, agents), as well as other devices, such as computer 126 (e.g., when it communicates with web app 120), and supports fair balancing. In various embodiments, load balancer 130 is a reverse proxy that load balances accepted connections internally to various microservices (described in more detail below), allowing for services provided by data platform 12 to scale up as more agents are added to the environment and/or as more entities subscribe to services provided by data platform 12. Example ways to implement load balancer 130 include, but are not limited to, using HaProxy, using nginx, and using elastic load balancing (ELB) services made available by Amazon.

Agent service 132 is a microservice that is responsible for accepting data collected from agents (e.g., provided by aggregator 114). In various embodiments, agent service 132 uses a standard secure protocol, such as HTTPS to communicate with aggregators (and, as applicable, agents), and receives data in an appropriate format such as Apache Avro. When agent service 132 receives an incoming connection, it can perform a variety of checks, such as to see whether the data is being provided by a current customer, and whether the data is being provided in an appropriate format. If the data is not appropriately formatted (and/or is not provided by a current customer), it may be rejected.

If the data is appropriately formatted, agent service 132 may facilitate copying the received data to a streaming data stable storage using a streaming service (e.g., Amazon Kinesis and/or any other suitable streaming service). Once the ingesting into the streaming service is complete, agent service 132 may send an acknowledgement to the data provider (e.g., data aggregator 114). If the agent does not receive such an acknowledgement, it is configured to retry sending the data to data platform 12. One way to implement agent service 132 is as a REST API server framework (e.g., Java DropWizard), configured to communicate with Kinesis (e.g., using a Kinesis library).

In various embodiments, data platform 12 uses one or more streams (e.g., Kinesis streams) for all incoming customer data (e.g., including data provided by data aggregator 114 and data aggregator 128), and the data is sharded based on the node (also referred to herein as a "machine") that originated the data (e.g., node 116 vs. node 122), with each node having a globally unique identifier within data platform 12. Multiple instances of agent service 132 can write to multiple shards.

Kinesis is a streaming service with a limited period (e.g., 1-7 days). To persist data longer than a day, the data may be copied to long term storage 42 (e.g., S3). Data loader 136 is a microservice that is responsible for picking up data from a data stream (e.g., a Kinesis stream) and persisting it in long term storage 42. In one example embodiment, files collected by data loader 136 from the Kinesis stream are placed into one or more buckets, and segmented using a combination of a customer identifier and time slice. Given a particular time segment, and a given customer identifier, the corresponding file (stored in long term storage) contains five minutes (or another appropriate time slice) of data collected at that specific customer from all of the customer's nodes. Data loader 136 can be implemented in any appropriate programming language, such as Java or C, and can be configured to use a Kinesis library to interface with Kinesis. In various embodiments, data loader 136 uses the Amazon Simple Queue Service (SQS) (e.g., to alert DB loader 140 that there is work for it to do).

DB loader 140 is a microservice that is responsible for loading data into an appropriate data store 30, such as SnowflakeDB or Amazon Redshift, using individual per-customer databases. In particular, DB loader 140 is configured to periodically load data into a set of raw tables from files created by data loader 136 as per above. DB loader 140 manages throughput, errors, etc., to make sure that data is loaded consistently and continuously. Further, DB loader 140 can read incoming data and load into data store 30 data that is not already present in tables of data store 30 (also referred to herein as a database). DB loader 140 can be implemented in any appropriate programming language, such as Java or C, and an SQL framework such as jOOQ (e.g., to manage SQLs for insertion of data), and SQL/JDBC libraries. In some examples, DB loader 140 may use Amazon S3 and Amazon Simple Queue Service (SQS) to manage files being transferred to and from data store 30.

Customer data included in data store 30 can be augmented with data from additional data sources, such as AWS CloudTrail and/or other types of external tracking services. To this end, data platform may include a tracking service analyzer 144, which is another microservice. Tracking service analyzer 144 may pull data from an external tracking service (e.g., Amazon CloudTrail) for each applicable customer account, as soon as the data is available. Tracking service analyzer 144 may normalize the tracking data as applicable, so that it can be inserted into data store 30 for later querying/analysis. Tracking service analyzer 144 can be written in any appropriate programming language, such as Java or C. Tracking service analyzer 144 also makes use of SQL/JDBC libraries to interact with data store 30 to insert/query data.

As described herein, data platform 12 can model activities that occur within datacenters, such as datacenters 104 and 106. The model may be stable over time, and differences, even subtle ones (e.g., between a current state of the datacenter and the model) can be surfaced. The ability to surface such anomalies can be particularly beneficial in datacenter environments where rogue employees and/or external attackers may operate slowly (e.g., over a period of months), hoping that the elastic nature of typical resource use (e.g., virtualized servers) will help conceal their nefarious activities.

Using techniques described herein, data platform 12 can automatically discover entities (which may implement compute assets 16) deployed in a given datacenter. Examples of entities include workloads, applications, processes, machines, virtual machines, containers, files, IP addresses, domain names, and users. The entities may be grouped together logically (into analysis groups) based on behaviors, and temporal behavior baselines can be established. In particular, using techniques described herein, periodic graphs can be constructed, in which the nodes are applicable logical entities, and the edges represent behavioral relationships between the logical entities in the graph. Baselines can be created for every node and edge.

Communication (e.g., between applications/nodes) is one example of a behavior. A model of communications between processes is an example of a behavioral model. As another example, the launching of applications is another example of a behavior that can be modeled. The baselines may be periodically updated (e.g., hourly) for every entity. Additionally or alternatively, the baselines may be continuously updated in substantially real-time as data is collected by agents. Deviations from the expected normal behavior can then be detected and automatically reported (e.g., as anomalies or threats detected). Such deviations may be due to a desired change, a misconfiguration, or malicious activity. As applicable, data platform 12 can score the detected deviations (e.g., based on severity and threat posed). Additional examples of analysis groups include models of machine communications, models of privilege changes, and models of insider behaviors (monitoring the interactive behavior of human users as they operate within the datacenter).

Two example types of information collected by agents are network level information and process level information. As previously mentioned, agents may collect information about every connection involving their respective nodes. And, for each connection, information about both the server and the client may be collected (e.g., using the connection-to-process identification techniques described above). DNS queries and responses may also be collected. The DNS query information can be used in logical entity graphing (e.g., collapsing many different IP addresses to a single service—e.g., s3.amazon.com). Examples of process level information collected by agents include attributes (user ID, effective user ID, and command line). Information such as what user/application is responsible for launching a given process and the binary being executed (and its SHA-256 values) may also provided by agents.

The dataset collected by agents across a datacenter can be very large, and many resources (e.g., virtual machines, IP addresses, etc.) are recycled very quickly. For example, an IP address and port number used at a first point in time by a first process on a first virtual machine may very rapidly be used (e.g., an hour later) by a different process/virtual machine.

Embodiments of data platform 12 may be built using any suitable infrastructure as a service (IaaS) (e.g., AWS). For example, data platform 12 can use Simple Storage Service (S3) for data storage, Key Management Service (KMS) for managing secrets, Simple Queue Service (SQS) for managing messaging between applications, Simple Email Service (SES) for sending emails, and Route 53 for managing DNS. Other infrastructure tools can also be used. Examples include: orchestration tools (e.g., Kubernetes or Mesos/Marathon), service discovery tools (e.g., Mesos-DNS), service load balancing tools (e.g., marathon-LB), container tools (e.g., Docker or rkt), log/metric tools (e.g., collectd, fluentd, kibana, etc.), big data processing systems (e.g., Spark, Hadoop, AWS Redshift, Snowflake etc.), and distributed key value stores (e.g., Apache Zookeeper or etcd2).

As previously mentioned, in various embodiments, data platform 12 may make use of a collection of microservices. Each microservice can have multiple instances, and may be configured to recover from failure, scale, and distribute work amongst various such instances, as applicable. For example, microservices are auto-balancing for new instances, and can distribute workload if new instances are started or existing instances are terminated. In various embodiments, microservices may be deployed as self-contained Docker containers. A Mesos-Marathon or Spark framework can be used to deploy the microservices (e.g., with Marathon monitoring and restarting failed instances of microservices as needed). The service etcd2 can be used by microservice instances to discover how many peer instances are running, and used for calculating a hash-based scheme for workload distribution. Microservices may be configured to publish various health/status metrics to either an SQS queue, or etcd2, as applicable. In some examples, Amazon DynamoDB can be used for state management.

Additional information on various microservices used in embodiments of data platform 12 is provided below.

Graph generator 146 is a microservice that may be responsible for generating raw behavior graphs on a per customer basis periodically (e.g., once an hour). In particular, graph generator 146 may generate graphs of entities (as the nodes in the graph) and activities between entities (as the edges). In various embodiments, graph generator 146 also performs other functions, such as aggregation, enrichment (e.g., geolocation and threat), reverse DNS resolution, TF-IDF based command line analysis for command type extraction, parent process tracking, etc.

Graph generator 146 may perform joins on data collected by the agents, so that both sides of a behavior are linked. For example, suppose a first process on a first virtual machine (e.g., having a first IP address) communicates with a second process on a second virtual machine (e.g., having a second IP address). Respective agents on the first and second virtual machines may each report information on their view of the communication (e.g., the PID of their respective processes, the amount of data exchanged and in which direction, etc.). When graph generator performs a join on the data provided by both agents, the graph will include a node for each of the processes, and an edge indicating communication between them (as well as other information, such as the directionality of the communication—i.e., which process acted as the server and which as the client in the communication).

In some cases, connections are process to process (e.g., from a process on one virtual machine within the cloud environment associated with entity A to another process on a virtual machine within the cloud environment associated with entity A). In other cases, a process may be in communication with a node (e.g., outside of entity A) which does not have an agent deployed upon it. As one example, a node within entity A might be in communication with node 172, outside of entity A. In such a scenario, communications with node 172 are modeled (e.g., by graph generator 146) using the IP address of node 172. Similarly, where a node within entity A does not have an agent deployed upon it, the IP address of the node can be used by graph generator in modeling.

Graphs created by graph generator 146 may be written to data store 30 and cached for further processing. A graph may be a summary of all activity that happened in a particular time interval. As each graph corresponds to a distinct period of time, different rows can be aggregated to find summary information over a larger timestamp. In some examples, picking two different graphs from two different timestamps can be used to compare different periods. If necessary, graph generator 146 can parallelize its workload (e.g., where its backlog cannot otherwise be handled within a particular time period, such as an hour, or if is required to process a graph spanning a long time period).

Graph generator 146 can be implemented in any appropriate programming language, such as Java or C, and machine learning libraries, such as Spark's MLLib. Example ways that graph generator computations can be implemented include using SQL or Map-R, using Spark or Hadoop.

SSH tracker 148 is a microservice that may be responsible for following ssh connections and process parent hierarchies to determine trails of user ssh activity. Identified ssh trails are placed by the SSH tracker 148 into data store 30 and cached for further processing.

SSH tracker 148 can be implemented in any appropriate programming language, such as Java or C, and machine libraries, such as Spark's MLLib. Example ways that SSH tracker computations can be implemented include using SQL or Map-R, using Spark or Hadoop.

Threat aggregator 150 is a microservice that may be responsible for obtaining third party threat information from various applicable sources, and making it available to other micro-services. Examples of such information include reverse DNS information, GeoIP information, lists of known bad domains/IP addresses, lists of known bad files, etc. As applicable, the threat information is normalized before insertion into data store 30. Threat aggregator 150 can be implemented in any appropriate programming language, such as Java or C, using SQL/JDBC libraries to interact with data store 30 (e.g., for insertions and queries).

Scheduler 152 is a microservice that may act as a scheduler and that may run arbitrary jobs organized as a directed graph. In some examples, scheduler 152 ensures that all jobs for all customers are able to run during a given time interval (e.g., every hour). Scheduler 152 may handle errors and retrying for failed jobs, track dependencies, manage appropriate resource levels, and/or scale jobs as needed. Scheduler 152 can be implemented in any appropriate programming language, such as Java or C. A variety of components can also be used, such as open source scheduler frameworks (e.g., Airflow), or AWS services (e.g., the AWS Data pipeline) which can be used for managing schedules.

Graph Behavior Modeler (GBM) 154 is a microservice that may compute various types of graphs. For example, GBM 154 can be used to find clusters of nodes in a graph that should be considered similar based on some set of their properties and relationships to other nodes. As described herein, the clusters and their relationships can be used to provide visibility into a datacenter environment without requiring user specified labels. GBM 154 may track such clusters over time persistently, allowing for changes to be detected and alerts to be generated.

GBM 154 may take as input a raw graph (e.g., as generated by graph generator 146). Nodes are actors of a behavior, and edges are the behavior relationship itself. For example, in the case of communication, example actors include processes, which communicate with other processes. The GBM 154 clusters the raw graph based on behaviors of actors and produces a summary (the graph). The graph may summarize behavior at a datacenter level. The GBM 154 also produces "observations" that represent changes detected in the datacenter. Such observations may be based on differences in cumulative behavior (e.g., the baseline) of the datacenter with its current behavior. The GBM 154 can be implemented in any appropriate programming language, such as Java, C, or Golang, using appropriate libraries (as applicable) to handle distributed graph computations (handling large amounts of data analysis in a short amount of time). Apache Spark is another example tool that can be used to compute graphs. The GBM 154 can also take feedback from users and adjust the model according to that feedback. For example, if a given user is interested in relearning behavior for a particular entity, the GBM 154 can be instructed to "forget" the implicated part of the graph.

GBM runner 156 is a microservice that may be responsible for interfacing with GBM 154 and providing GBM 154 with raw graphs (e.g., using a query language, such as SQL, to push any computations it can to data store 30). GBM runner 156 may also insert graph output from GBM 154 to data store 30. GBM runner 156 can be implemented in any appropriate programming language, such as Java or C, using SQL/JDBC libraries to interact with data store 30 to insert and query data.

Alert generator 158 is a microservice that may be responsible for generating alerts. Alert generator 158 may examine observations (e.g., produced by GBM 154) in aggregate, deduplicate them, and score them. Alerts may be generated for observations with a score exceeding a threshold. Alert generator 158 may also compute (or retrieve, as applicable) data that a customer (e.g., user A or user B) might need when reviewing the alert.

Alert generator 158 can be implemented in any appropriate programming language, such as Java or C, using SQL/JDBC libraries to interact with data store 30 to insert and query data. In various embodiments, alert generator 158 also uses one or more machine learning libraries, such as Spark's MLLib (e.g., to compute scoring of various observations). Alert generator 158 can also take feedback from users about which kinds of events are of interest and which to suppress.

QsJobServer 160 is a microservice that may look at all the data produced by data platform 12 for an hour, and compile a materialized view (MV) out of the data to make queries faster. The MV helps make sure that the queries customers most frequently run, and data that they search for, can be easily queried and answered. QsJobServer 160 may also precompute and cache a variety of different metrics so that they can quickly be provided as answers at query time. QsJobServer 160 can be implemented using any appropriate programming language, such as Java or C, using SQL/JDBC libraries. In some examples, QsJobServer 160 is able to compute an MV efficiently at scale, where there could be a large number of joins. An SQL engine, such as Oracle, can be used to efficiently execute the SQL, as applicable.

Alert notifier 162 is a microservice that may take alerts produced by alert generator 158 and send them to customers' integrated Security Information and Event Management (SIEM) products (e.g., Splunk, Slack, etc.). Alert notifier 162 can be implemented using any appropriate programming language, such as Java or C. Alert notifier 162 can be configured to use an email service (e.g., AWS SES or pagerduty) to send emails. Alert notifier 162 may also provide templating support (e.g., Velocity or Moustache) to manage templates and structured notifications to SIEM products.

Reporting module 164 is a microservice that may be responsible for creating reports out of customer data (e.g., daily summaries of events, etc.) and providing those reports to customers (e.g., via email). Reporting module 164 can be implemented using any appropriate programming language, such as Java or C. Reporting module 164 can be configured to use an email service (e.g., AWS SES or pagerduty) to send emails. Reporting module 164 may also provide templating support (e.g., Velocity or Moustache) to manage templates (e.g., for constructing HTML-based email).

Web app 120 is a microservice that provides a user interface to data collected and processed on data platform 12. Web app 120 may provide login, authentication, query, data visualization, etc. features. Web app 120 may, in some embodiments, include both client and server elements. Example ways the server elements can be implemented are using Java DropWizard or Node.Js to serve business logic, and a combination of JSON/HTTP to manage the service. Example ways the client elements can be implemented are using frameworks such as React, Angular, or Backbone. JSON, jQuery, and JavaScript libraries (e.g., underscore) can also be used.

Query service 166 is a microservice that may manage all database access for web app 120. Query service 166 abstracts out data obtained from data store 30 and provides a JSON-based REST API service to web app 120. Query service 166 may generate SQL queries for the REST APIs that it receives at run time. Query service 166 can be implemented using any appropriate programming language, such as Java or C and SQL/JDBC libraries, or an SQL framework such as jOOQ. Query service 166 can internally make use of a variety of types of databases, including a relational database engine 168 (e.g., AWS Aurora) and/or data store 30 to manage data for clients. Examples of tables that query service 166 manages are OLTP tables and data warehousing tables.

Cache 170 may be implemented by Redis and/or any other service that provides a key-value store. Data platform 12 can use cache 170 to keep information for frontend services about users. Examples of such information include valid tokens for a customer, valid cookies of customers, the last time a customer tried to login, etc.

Figure 1E:
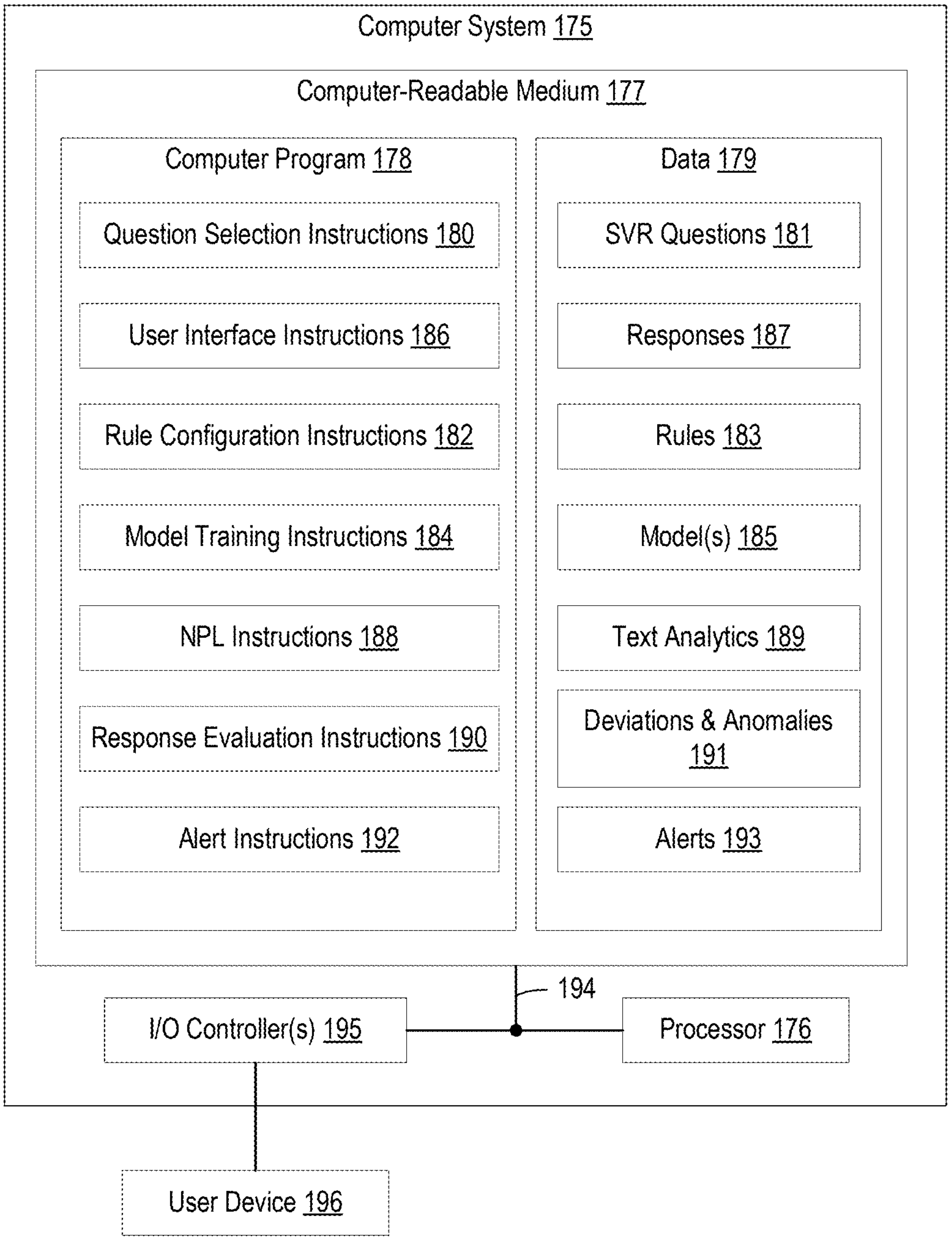
FIG. 1E is a block diagram of a computer system configured to evaluate responses to a report.

FIG. 1E is a block diagram of a computer system 175 configured to evaluate responses to a report (e.g., a site visit report (SVR)). Computer system 175 may be further configured to configure the report with questions. Computer system 175 may be further configured to train a model for use in evaluating the responses to the report. Computer system 175 may represent an example embodiment or implementation of a report engine described with reference to one or more other examples herein.

Computer system 175 includes an instruction processor 176 to execute instructions of a computer program 178 encoded within a computer-readable medium 177. Computer-readable medium 177 further includes data 179, which may be used by processor 176 during execution of computer program 178 and/or generated by processor 176 during execution of computer program 178. Computer-readable medium 177 may include a transitory or non-transitory computer-readable medium.

In the example of FIG. 1E, computer program 178 includes question selection instructions 180 to cause processor 176 to select questions 181 (and, in some cases, sub-questions) to include in a SRV. Computer program 178 further includes user interface instructions 186 to cause processor 176 to present questions 181 on a user device and receive responses 187 (e.g., user-selected answers and natural language comments) from the user device.

Computer program 178 further includes rule configuration instructions 182 to cause processor 176 to configure rules 183 with which to process responses 187 to questions 181 (e.g., to detect protocol deviations), such as described in one or more examples above. Computer program 178 further includes model training instructions 184 to cause processor 176 to train a model 185 to detect anomalies from responses 187.

Model training instructions 184 may include instructions to cause processor 176 to train a probabilistic topic model to detect topics from natural language notes. Model training instructions 184 may include instructions to cause processor 176 to train a sentiment model to detect sentiments from natural language notes. Computer program 178 further includes natural language processing (NPL) instructions 188 to cause processor 176 to extract text analytics 189 (e.g., sentiment analytics and/or topical analytics) from natural language comments of responses 187, such as described in one or more examples above. Computer program 178 further includes response evaluation instructions 190 to cause processor 176 to evaluate responses 187 based on rules 183, analytics 189, and model 185 to identify deviations and anomalies 191. Computer program 178 further includes alert instructions 192 to cause processor 176 to generate alerts 193 based on deviations and anomalies 191. Computer system 175 further includes communications infrastructure 194 to communicate amongst devices and/or resources of computer system 175. Computer system 175 may include one or more input/output (I/O) devices and/or controllers 195 to interface with one or more other systems, such as to interface with a user device 196 of a site monitor, a sponsor, and/or an investigator associated with a clinical study.

Advantages and features of the present disclosure can be further described by the following statements:

1. A computer-system-implemented method for remote management of clinical research using a multi-tenant clinical research platform, the method comprising: granting a user having proper credentials access to the platform through a login process to manage one or more clinical study visits to one or more clinical research sites, the platform configured to access, via a first network connection, an electronic data capture (EDC) data store containing EDC data for a plurality of digitized clinical studies each having a set of clinical study protocols, the platform further configured to access, via a second network connection, an electronic medical record (EMR) data store containing EMR data about a plurality of patients, where the EMR data store and the EDC data store are separate from one another and implement different data specifications, the platform further configured to access and use mappings between EDC data for the one or more clinical study visits and EMR data associated with the one or more clinical study visits; receiving, via a user interface, a request from the user to access a patient record for a patient's clinical study visit to a clinical research site; retrieving and using, by the platform, the patient record to access EDC data for the patient's clinical study visit to the clinical research site; retrieving, by the platform and based on the mappings, EMR data associated with the patient's clinical study visit to the clinical research site; displaying, together via the user interface, the EDC data for the patient's clinical study visit to the clinical research site and the EMR data associated with the patient's clinical study visit to the clinical research site; providing, via the user interface and in association with the displayed EDC data and EMR data, a review tool as part of a clinical research review workflow; receiving user input via the review tool; annotating, based on the user input, the EDC data for the patient's clinical study visit.

2. The computer-system-implemented method of any of the preceding statements, wherein retrieving the EMR data associated with the patient's clinical study visit to the clinical research site comprises selecting and requesting the EMR data based on a context of the EDC data.

3. The computer-system-implemented method of any of the preceding statements, wherein the EMR data store is implemented by an integrated data platform system configured to ingest raw EMR data from an EMR system of the clinical research site, transform the raw EMR data into United States Core Data for Interoperability (USCDI) format, and provide an interface through which the EMR data in USCDI format is accessible by the platform.

4. The computer-system-implemented method of any of the preceding statements, wherein the integrated data platform system is further configured to generate the mappings between the EDC data for the one or more clinical study visits and the EMR data associated with the one or more clinical study visits.

5. The computer-system-implemented method of any of the preceding statements, wherein the mappings comprise a mapping of a patient identifier for a patient represented in the EDC data to an EMR identifier for the patient represented in the EDC data.

6. The computer-system-implemented method of any of the preceding statements, wherein the mappings comprise a mapping of a clinical-study-protocol-defined data field represented in the EDC data to EDC data determined to be related to the data field.

7. The computer-system-implemented method of any of the preceding statements, wherein the mappings comprise a mapping of EDC data associated with a question in a clinical review workflow to EMR data determined to be related to the question.

8. The computer-system-implemented method of any of the preceding statements, wherein the platform is configured to prevent persistence of the EMR data retrieved by platform.

9. The computer-system-implemented method of any of the preceding statements, wherein the review tool comprises a user-selectable option to indicate a protocol deviation for the EDC data for the patient's clinical study visit to the clinical research site, based on a review of the EMR data associated with the patient's clinical study visit to the clinical research site.

10. The computer-system-implemented method of any of the preceding statements, wherein the review tool comprises a user-selectable option to indicate a verification of the EDC data for the patient's clinical study visit to the clinical research site, based on a review of the EMR data associated with the patient's clinical study visit to the clinical research site.

11. The computer-system-implemented method of any of the preceding statements, wherein the review tool comprises a user-selectable option to indicate non-compliance of the clinical review site for the EDC data for the patient's clinical study visit to the clinical research site, based on a review of the EMR data associated with the patient's clinical study visit to the clinical research site.

12. The computer-system-implemented method of any of the preceding statements, further comprising: analyzing, by the platform, the EDC data and the EMR data;

identifying, by the platform and based on the analyzing, a protocol deviation;

providing, by the platform, a notification of the protocol deviation by way of the user interface.

13. The computer-system-implemented method of any of the preceding statements, further comprising: analyzing, by the platform, the EDC data and the EMR data;

identifying, by the platform and based on the analyzing, a monitoring action to be taken;

providing, by the platform, a notification of the monitoring action by way of the user interface.

14. The computer-system-implemented method of any of the preceding statements, wherein a trained artificial intelligence model is used to analyze the EDC data and the EMR data and identify the monitoring action to be taken.

15. A multi-tenant clinical research platform system for remote management of clinical research sites, the system comprising: an integrated data platform system comprising at least a first processor and a first non-transitory computer-readable memory storing first instructions executable by the first processor to: access patient data from a clinical data repository; ingest, from one or more clinical research sites, electronic medical record (EMR) data associated with patients identified by the patient data; generate and store mappings between the patient data and the EMR data; provide an egress interface through which the EMR data is externally accessible; a source data management system communicatively coupled to the integrated data platform system by a secure network communication link and comprising at least a second processor and a second non-transitory computer-readable memory storing second instructions executable by the second processor to: grant a user having proper credentials access through a login process to manage one or more clinical study visits to the one or more clinical research sites; access, from the clinical data repository, electronic data capture (EDC) data for a patient; access, from the integrated data platform system, electronic medical record (EMR) data for the patient; integrate the EDC data and the EMR data for the patient into a clinical research review workflow; and provide, via a user interface, the clinical research review workflow with the integrated EDC data and EMR data.

16. The multi-tenant clinical research platform system of any of the preceding statements, wherein source data management system is configured to prevent persistence of the EMR data by the source data management system.

17. The multi-tenant clinical research platform system of any of the preceding statements, wherein the integrated data platform system is configured to transform the ingested EMR data into United States Core Data for Interoperability (USCDI) format.

18. The multi-tenant clinical research platform system of any of the preceding statements, wherein the mappings comprise a mapping of a patient identifier for a patient represented in the EDC data to an EMR identifier for the patient represented in the EDC data.

19. The multi-tenant clinical research platform system of any of the preceding statements, wherein the second instructions are further executable by the second processor to: provide, via the user interface and in association with the integrated EDC data and EMR data, a review tool as part of the clinical research review workflow; receive user input via the review tool; annotate, based on the user input, the EDC data for the patient.

20. A computer program product embodied in a non-transitory computer readable storage medium and comprising computer instructions for: granting a user having proper credentials access to a clinical research platform through a login process to manage one or more clinical study visits to one or more clinical research sites, the platform configured to access, via a first network connection, an electronic data capture (EDC) data store containing EDC data for a plurality of digitized clinical studies each having a set of clinical study protocols, the platform further configured to access, via a second network connection, an electronic medical record (EMR) data store containing EMR data about a plurality of patients, where the EMR data store and the EDC data store are separate from one another and implement different data specifications, the platform further configured to access and use mappings between EDC data for the one or more clinical study visits and EMR data associated with the one or more clinical study visits; receiving, via a user interface, a request from the user to access a patient record for a patient's clinical study visit to a clinical research site; retrieving and using, by the platform, the patient record to access EDC data for the patient's clinical study visit to the clinical research site; retrieving, by the platform and based on the mappings, EMR data associated with the patient's clinical study visit to the clinical research site; displaying, together via the user interface, the EDC data for the patient's clinical study visit to the clinical research site and the EMR data associated with the patient's clinical study visit to the clinical research site; providing, via the user interface and in association with the displayed EDC data and EMR data, a review tool as part of a clinical research review workflow; receiving user input via the review tool; annotating, based on the user input, the EDC data for the patient's clinical study visit.

21. A computer-system-implemented method for remotely monitoring source data of a clinical research site, the method comprising: accessing, from a first remote data store, electronic data capture (EDC) data associated with the clinical research site, the EDC data including a patient identifier for a patient participating in clinical research at the clinical research site and clinical research information about the patient; accessing, on-demand from a second remote data store and based on the EDC data, contextual electronic medical record (EMR) data associated with the patient and the clinical research site; displaying, on a user interface, the EDC data and the EMR data for review by a clinical research monitor.

22. The computer-system-implemented method of any of the preceding statements, wherein accessing the EMR data associated with the patient and the clinical research site comprises selecting and retrieving the EMR data based on a context of the EDC data displayed on the user interface.

23. The computer-system-implemented method of any of the preceding statements, wherein accessing the EMR data associated with the patient and the clinical research site comprises filtering out the EMR data associated with the patient and the clinical research site from EMR data associated with a plurality of patients participating in one or more clinical research studies at one or more clinical research sites.

24. The computer-system-implemented method of any of the preceding statements, wherein the filtering is based on the patient identifier.

25. The computer-system-implemented method of any of the preceding statements, wherein the filtering is based on patient demographic information.

26. The computer-system-implemented method of any of the preceding statements, further comprising: receiving user input by way of the user interface on which the EDC data and the EMR data are displayed; and sending, based on the user input, an EDC data update to the first data store.

27. The computer-system-implemented method of any of the preceding statements, wherein the second data store is implemented by a data management platform system that: ingests EMR data from a plurality of clinical research sites, the ingested EMR data including the EMR data associated with the patient and the clinical research site; standardizes the EMR data into United States Core Data for Interoperability (USCDI) format; and provides an interface through which the EMR data in USCDI format is externally accessible.

28. The computer-system-implemented method of any of the preceding statements, wherein the data management platform: ingests the EDC data from the first data store, the ingested EDC data including the patient identifier for the patient participating in clinical research at the clinical research site; and generates a mapping of the patient identifier to the ingested EMR data associated with the patient and the clinical research site.

29. The computer-system-implemented method of any of the preceding statements, wherein:

the EDC data and the EMR data are displayed on a user interface of a client computing device; the client computing device is configured to prevent persistence of the EDC data and the EMR data at the client computing device.

30. The computer-system-implemented method of any of the preceding statements, further comprising: analyzing the EDC data and the EMR data; identifying, based on the analyzing, a monitoring action to be taken; providing a notification of the monitoring action by way of the user interface.

31. The method of any of the preceding statements, wherein an artificial intelligence model is used to analyze the EDC data and the EMR data.

32. The computer-system-implemented method of any of the preceding statements, further comprising: analyzing the EMR data; identifying, based on the analyzing, a clinical research protocol deviation; providing a notification of the clinical research protocol deviation by way of the user interface.

Example methods, systems, apparatuses, and products for remote management (e.g., remote monitoring) of clinical research source data and/or clinical research sites are described herein, with reference to illustrative embodiments of the present disclosure. In some embodiments, the methods, systems, apparatuses, and products may be implemented using any of the configurations and/or components described above and illustrated in FIGS. 1A-1E.

Figure 2:
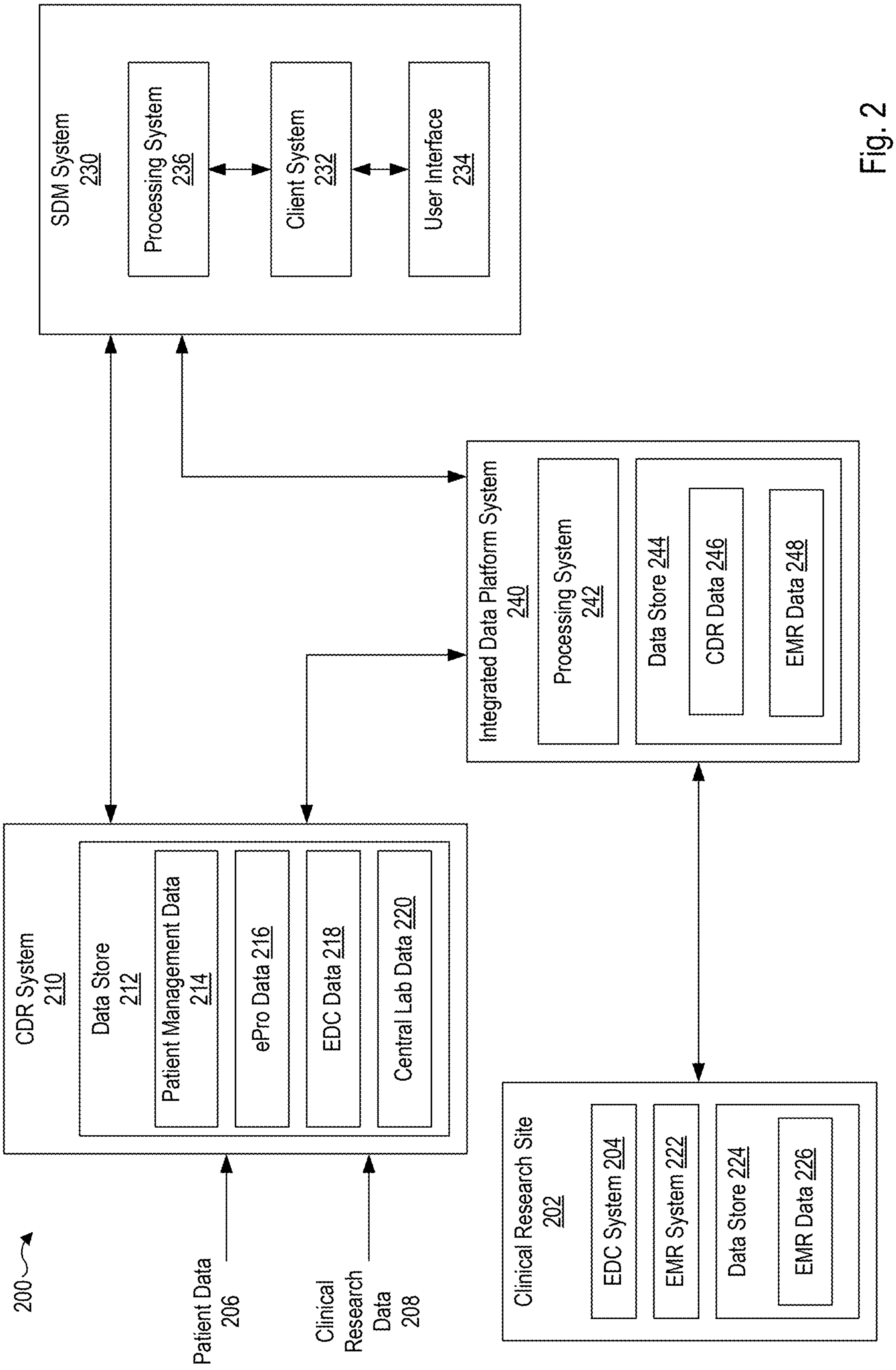
FIG. 2 illustrates an example system configured for remote management of clinical research.

FIG. 2 illustrates an example of a system 200 configured for remote management of clinical research source data and clinical research sites in accordance with some embodiments. System 200 includes various communicatively interconnected systems configured to perform one or more of the operations described herein. The systems may be implemented as one or more computer systems configured to perform the operations. Each system may be implemented in its own separate computing domain and may include one or more physical and/or virtual computing resources, such as physical computer processors, memory, data storage resources, and network interfaces. Any of the systems may be implemented using one or more components of data platform 12, cloud environment 14, data store 30, computing device 50, and/or computer system 175 described above.

One or more of the various systems shown in FIG. 2 may be interconnected using any suitable data communication technologies that allow controlled and protected transmission of data between systems. For example, two-way arrows shown in FIG. 2 represent network connections between systems, which may include any secure network connections such as wide area network connections, internet connections (e.g., HTTPS connections), secure communication links, virtual private networks, SSH connections, etc.

Clinical research is a component of medical and health research intended to produce evidence-based knowledge valuable for understanding human disease, preventing and treating illness, and promoting health. Clinical research involves systematic investigation of human health and disease through clinical studies such as clinical trials, observational studies, and epidemiological research conducted in accordance defined protocols. Clinical research aims to generate evidence-based data to advance medical knowledge, improve patient care, and support regulatory decision-making for new and existing therapies.

Some clinical research involves patient visits to clinical research sites such as medical centers, hospitals, private physician practices, and other healthcare facilities that conduct clinical studies in real-world settings. Clinical research site 202 represents any site at which clinical research is conducted, including any facility or other site that conducts one or more clinical studies in a real-world setting such as a setting in which clinical healthcare services are provided to patients.

As part of a clinical study conducted at clinical research site 202, a patient participating in the clinical study may visit clinical research site 202. For the visit, clinical study personnel (e.g., a study investigator) conduct protocol-specified procedures and assessments, which may include, for example, obtaining vital signs, conducting physical exams, collecting laboratory samples (e.g., blood draws, urine tests, etc.), conducting electrocardiograms (ECGs), imaging, or interviewing of the patient. Data associated with the procedures and assessments is collected via electronic platforms and/or paper forms in accordance with the study protocol. If patient-reported outcomes are required by the study protocol, the patient may complete questionnaires via electronic platforms or paper forms.

Data associated with the clinical study and the patient visit to clinical research site 202 is entered into an electronic data capture (EDC) system 204. For example, the patient and/or study personnel may enter collected data into EDC system 204 in any suitable way. EDC system 204 may provide an interface by which collected data is provided to the EDC system 204, such as electronic and/or paper documents (e.g., an electronic or paper case report form (CFR) such as a web-based form or other electronic form (eCRF)) that allows standardization, across patients, of the data that is collected for the clinical study. Data may be entered into EDC system 204 in any suitable way, including transcription, voice recordings, form-based data entry, collection of data from sensors or other devices, etc. EDC system 204 may be implemented onsite at the clinical research site 202 or offsite from the clinical research site 202, so long as an interface to the EDC system 204 is accessible to study personnel.

Data generated as part of clinical research, such as data generated in relation to patient visits to clinical research site 202 for clinical research activities, is referred to as clinical research source data. The types of clinical research source data collected and recorded in EDC system 204, for a clinical study, are defined by the clinical study protocol.

The collected clinical research source data may include patient data and/or clinical research data. Patient data may include any information about the patient participating in the clinical study, such as patient identifying data, patient demographic information, informed consent data representing consent given by the patient, patient medical history data, and electronic patient-reported outcomes (ePRO) data. Clinical research data may include any data collected in association with a patient visit (e.g., during or after the visit) and recorded in EDC system 204 as part of a clinical study. Examples of clinical research data include, without limitation, vital signs, physical exam observations, laboratory sample data, lab results, ECG data, imaging data, procedural information, or any other information that is collected in association with the patient visit and entered in EDC system 204.

In FIG. 2, patient data 206 and clinical research data 208 represent source data collected in association with a patient visit to clinical research site 202 and entered in EDC system 204. The collected data is provided to and managed in a clinical data repository (CDR) system 210. CDR system 210 may be configured to receive, store, and manage the data in a repository such as data store 212. Data store 212 may be implemented as any suitable data storage structure, such as a database, that is configured to store data in accordance with a clinical study protocol and applicable regulations for storage of clinical research source data.

While FIG. 2 shows CDR system 210 to include one data store 212, in some embodiments, CDR system 210 may store and manage clinical research source data for a plurality of clinical studies and associated clinical study visits to a plurality of clinical research sites such as clinical research site 202. Thus, CDR system 210 may be configured to function as a multi-tenant clinical search platform that receives, stores, manages, and provides controlled access to clinical research source data for a plurality of clinical studies.

As shown in FIG. 2, data store 212 may store various types of patient data 206 and clinical research data 208 such as patient management data 214, ePRO data 216, EDC data 218, and central lab data 220. Patient management data 214 may represent patient consent data and patient management data (e.g., patient data used by a clinical trial management system), ePRO data 216 may represent patient-provided outcomes, EDC data 218 may represent clinical research information recorded in EDC system 204, and central lab data 220 may represent lab data received from laboratories and/or clinical research sites in association with clinical research. EDC data 218 may include information about patient observations, clinical assessments, adverse events, laboratory results, and/or other study-specific data points entered in EDC system 204 by study personnel.

The integrity and credibility of clinical research source data such as EDC data 218 is important for correct and reliable clinical study outcomes. Monitoring and validation of clinical research source data such as EDC data 218, as well as the protocols followed to collect the data, are essential in clinical research to ensure data accuracy, integrity, and compliance with regulatory standards and best practices. Monitoring of the data helps identify and resolve discrepancies, missing data, and protocol deviations in the data and/or in the collection and recording of the data. Validation of the data helps maintain consistency and reliability across various clinical research sites while minimizing errors that could impact clinical study outcomes. Properly monitored and validated EDC data 218 enhances data credibility, supports regulatory submissions, and ensures that clinical study results are correctly based on the clinical study protocols.

A clinical study monitor, such as a contract research associate (CRA), plays an important role in overseeing the accuracy, completeness, and compliance of EDC data in clinical research. A monitor may be granted access to CDR system 210, specifically to clinical research source data associated with a clinical study and associated visits to one or more clinical research sites. The monitor may check the clinical research source data such as by visiting clinical research sites to verify that data entered in the EDC system aligns with source documents maintained at the clinical research sites, ensuring adherence to study protocols, good clinical practices, and regulatory requirements. A monitor may review case report forms (CRFs), resolve data discrepancies through query management, and ensure timely reporting of adverse events. A monitor may also provide training and guidance to study personnel on data entry best practices and compliance standards. Such monitoring activities performed by a clinical study monitor may help safeguard the reliability of clinical study data and clinical study results.

One way of monitoring a clinical research site and its clinical research source data includes a clinical study monitor scheduling a visit to the clinical research site, obtaining onsite access to electronic medical records (EMR) data of the clinical research site, and using the EMR data to check and validate EDC data and/or to identify discrepancies or protocol deviations. The EMR data is generated and maintained by the clinical research site in accordance with the site's own practices and data specifications. For example, clinical research site 202 may include an EMR system 222 that is used by site personnel (e.g., healthcare providers such as physicians, nurses, staff, etc.) to collect and record medical/health information of patients in association with patient visits. This information may be stored in data store 224 as EMR data 226. Data store 224 may include any data storage structure, such as a database, and EMR data 226 may be stored in accordance with any acceptable electronic medical record format. EMR data 226 may include digital health information collected and maintained by healthcare providers, such as healthcare providers who provide healthcare services at a healthcare site that is also functioning as a clinical research site. EMR data 226 may include vital signs, physical exam observations, laboratory sample data, lab results, ECG data, imaging data, procedural information, or any other information that is collected in association with a patient visit and entered in the EMR system 222.

The data stores in which EDC data and EMR data are stored are separate from one another. The separation may be a physical and/or a logical separation. For example, data store 212 may be referred to as an EDC data store and may be maintained at a first computing domain (as part of CDR system 210) on a first set of physical computing and storage machines. Data store 224 may be referred to as an EMR data store and may be maintained at a second computing domain (as part of EMR system 222 of clinical research site 202) on a second set of physical computing and storage machines, which second computing domain and second set of physical computing and storage machines are separate from and independent of the first computing domain and first set of physical computing and storage machines. EDC data and EMR data may be maintained in separate data stores for one or more reasons, such as complying with regulatory requirements (e.g., data privacy requirements), following best practices for managing medical/health information and/or clinical research, and allowing for independence of clinical research data.

The data stores in which EDC data and EMR data are stored implement different data specifications. For example, data store 212 may use a first data specification such as a first set of standards and rules that define the structure, format, and content of EDC data, and data store 224 may use a second data specification that is different from the first data specification. For instance, the second data specification may include a second set of standards and rules that define the structure, format, and/or content of EMR data, which are different from the structure, format, and/or content of EDC data.

EMR data such as EMR data 226 differs from EDC data such as EDC data 218 in one or more ways. EDC data is collected specifically for clinical research studies and adheres to defined data specifications that are based on study protocols (e.g., protocol-defined case report forms (CRFs), whereas EMR data originates from routine clinical care and patient management within healthcare service sites. EDC data is structured, standardized, and optimized for regulatory compliance and statistical analysis. In contrast, EMR data is more variable, often contains unstructured data (e.g., physician notes), and is tailored for clinical decision-making rather than clinical research. EDC data may be captured in real time during clinical studies, with strict version control and audit trails ensuring data traceability. EMR data, however, evolves over time, reflecting a patient's longitudinal health record, and may contain retrospective modifications or corrections. EDC data may include patient identifiers used to identify patients participating in clinical research, whereas EMR data may use different identifiers, such as EMR identifiers, to identify all patients provided with healthcare services at a clinical research site, including patients participating in clinical research and patients not participating in clinical research at the site. EDC data and EMR data are maintained in distinct and separate data stores and often use different data formats and schema, as described above.

A monitor who visits clinical research site 202 and is given onsite access to EMR system 222 and/or EMR data 226 may use the EMR data to check the EDC data for compliance with study protocols. For example, while onsite, the monitor may use EMR data 226 to determine whether clinical study protocols were followed in the collection of EDC data, identify protocol deviations, identify data discrepancies between EDC data and EMR data, identify EDC data entry errors, validate EDC data, identify adverse events, determine whether adverse events are indicated in the EDC data, etc. The monitor may implement actions to flag and/or resolve identified protocol deviations, data discrepancies, adverse events, and data entry errors. The monitor may also validate EDC data after determining that the EMR data supports the EDC data and indicates that study protocols were followed in the collection of the EDC data.

A visit by a monitor to clinical research site 202 typically requires that the monitor schedule, in advance, the visit with the operator of clinical research site 202, and that the monitor schedule and obtain time-constrained access to the EMR system 222 and EMR data 226. One purpose of the time-constrained onsite access to the EMR system 222 and EMR data 226 is to protect the EMR data 226 by controlling access to it in accordance with regulatory requirements and best practices. The monitor must travel to the location of clinical research site 202 and be onsite to conduct monitoring activities that use EMR data 226. While these requirements control access to protected EMR data 226, they create time constraints and logistical burdens on both the clinical research monitor and the operator of clinical research site 202. The operator must schedule visits and set up EMR data access permissions for all monitors who want to access and use EMR data to monitor clinical studies conducted at clinical research site 202. The monitoring activities performed during those visits may use site resources that could otherwise be used for normal healthcare operations of the site. Such constraints and burdens may increase costs associated with clinical research, limit the scale at which a clinical research site can help with clinical studies, and/or limit the scale at which a clinical research monitor can monitor clinical studies.

A source data management (SDM) system 230 is configured to provide remote management of clinical research source data and/or clinical research sites, which may address one or more issues associated with onsite monitoring of a clinical research site. For example, a clinical research monitor, such as a CRA, may access and use one or more monitoring tools (e.g., data review tools) provided by SDM system 230 to remotely monitor and manage clinical research sites and clinical research source data such as EDC data 218. Using monitoring tools and workflows provided by SDM system 230, the monitor may access clinical research source data, such as EDC data 218, maintained by CDR system 210. In the context of accessing and reviewing the clinical research source data, the monitor, while offsite of clinical research sites, may remotely access and use EMR data such as EMR data 226 to determine whether clinical study protocols were followed in the collection of the clinical research source data, identify protocol deviations, identify data discrepancies between source data and EMR data, identify source data entry errors, identify adverse events, validate the source data, annotate the source data, etc.

To facilitate remote monitoring activities, SDM system 230 provides a user interface with which a clinical research monitor may interact to access monitoring tools, workflows, and data. A monitor may utilize client system 232 to access and interact with user interface 234 of SDM system 230. Client system 232 may include any suitable computing device (e.g., a laptop computer, a tablet computer, a smartphone device, or any computer) configured to access and/or provide user interface 234. User interface 234 may be any interface through which the monitor may interact with client system 232 and/or SDM system 230. For example, user interface 234 may include a web interface such as web portal accessible by a web browser, or user interface 234 may include an application portal accessible by way of an application client running on client system 232.

SDM system 230 includes a processing system 236 configured to access data from multiple different sources and provide the accessed data for monitoring activities and workflows, such as by providing select data on user interface 234 for review by a monitor. SDM system 230 is configured to access and provide the data in ways that address one or more technical challenges associated with providing remote, on-demand access to data from different data stores and having different data specifications, and in particular doing this while controlling access to protected health care information included in the data and/or data stores.

To this end, processing system 236 is configured to access clinical research source data from a first data store such as data store 212 of CDR system 210. Certain examples described herein refer to processing system 236 accessing patient data such as patient management data 214 and EDC data such as EDC data 218 from a first data store such as data store 212. However, it will be understood that processing system 236 may access any data from data store 212 of CDR system 210 in other embodiments.

CDR system 210 may provide an application programming interface (API) and/or other mechanism(s) by way of which SDM system 230 may access patient and EDC data 218. The access may include requesting and retrieving specific instances of patient data and EDC data 218, such as patient and EDC data associated with a particular patient participating in a particular clinical study, patient and EDC data collected at a particular clinical research site for a particular clinical study, and/or patient and EDC data associated with a particular patient visit to a particular clinical research site.

In addition or alternative to accessing patient and EDC data from data store 212 of CDR system 210, in some embodiments SDM system 230 may access patient and/or EDC data from a data store of an intermediary data platform system such as integrated data platform (IDP) system 240. Thus, processing system 226 of SDM system 230 may be configured to access clinical research source data such as patient and EDC data directly from CDR system 210, indirectly from CDR system 210 via IDP system 240, or a combination of both directly from CDR system 210 and indirectly from CDR system 210 via IDP system 240 (e.g., where a subset of data is accessed directly from CDR system 210 and another subset of data is accessed indirectly from CDR system 210 via IDP system 240).

In addition to accessing clinical research source data such as patient and EDC data from the first data store, processing system 236 is configured to access EMR data from a second data store such as a data store of IDP system 240. IDP system 240 will now be described in detail. While the description of IDP system 240 is provided in the context of accessing data from CDR system 210 and clinical research site 202, this is illustrative. IDP system 240 may be configured to function as a multi-tenant clinical search data integration platform that receives, stores, manages, and provides controlled access to 1) source data such as patient data for a plurality of clinical studies and associated clinical study visits to a plurality of clinical research sites such as clinical research site 202 and/or 2) EMR data accessed from the plurality of clinical research sites. Thus, IDP system 240 may ingest EMR data from multiple clinical research sites. The ingested EMR data may include data associated with multiple clinical studies at multiple clinical research sites. IDP system 240 may provide a multi-tenant platform configured to manage access to appropriate patient data and EMR data.

IDP system 240 may ingest, process, and prepare EMR data for access by SDM system 230. IDP system 240 may include a processing system 242 configured to perform operations of IDP system 240 described herein, including data ingestion, processing, storage, and providing operations.

IDP system 240 may be configured to ingest, from data store 224 of clinical research site 202, only a subset of the EMR data 226 in data store 224, which subset of EMR data 226 is EMR data associated with patients who are participating in clinical studies and have provided appropriate consent. In some examples, the subset of EMR data may be even more granularly identified and may include, for example, only EMR data associated with specific patient visits to specific clinical research sites.

To enable the identification and ingestion of only some EMR data 226, IDP system 240 may be configured to ingest clinical research source data from CDR system 210. The ingested data may be referred to as CDR data and may include data maintained by CDR system 210, such as patient identifiers used in clinical studies, information about patients such as patient consent, demographic, and health information, EDC data, and data representative of clinical studies such as data representing clinical study protocols. In some embodiments, the ingested CDR data may include information about patient visits to clinical trial sites, such as dates of patient visits to specific sites. Such patient data may be accessed from patient management data 214 and/or EDC data 218 in data store 212. IDP system 240 may process and store the accessed CDR data in data store 244 as CDR data 246.

IDP system 240 may be configured to ingest EMR data from multiple distinct clinical research sites such as clinical research site 202. As described above, the ingestion of the EMR data may be targeted to ingest only EMR data associated with patients participating in clinical research. For example, IDP system 240 may request and receive EMR data associated with patient identifiers and/or other information about patients participating in clinical research, which identifiers and/or information has been accessed from CDR system 210 and stored as CDR data 246. In other embodiments, IDP system 240 may more broadly ingest EMR data from a clinical research site, process it to identify a subset of the EMR data that is associated with patients participating in clinical research and store only the identified subset of the EMR data without persisting EMR data that is not identified as being associated with patients participating in clinical research. The processing to identify the subset of the EMR data may include identifying EMR data associated with patient identifiers and/or other information about patients participating in clinical research.

IDP system 240 may store EMR data associated with patients participating in clinical research in data store 244 as EMR data 248. While CDR data 246 and EMR data 248 are shown to be stored in data store 244, CDR data 246 and EMR data 248 may be stored in distinct and separate data stores (e.g., databases) of IDP system 240.

Data store 244 is separate from data store 212 and data store 224. The separation may be a physical and/or a logical separation. For example, data store 244, which may be referred to as an EMR data store, may be maintained at a computing domain (as part of IDP system 240) on a set of physical computing and storage machines that are different from the computing domains and sets of physical computing and storage machines at which data store 212 and data store 224 are implemented.

Data store 244 may implement a different data specification than the data specifications implemented by data store 212 and/or data store 224. For example, data store 244 may use a data specification such as a set of standards and rules that define the structure, format, and content of EMR data, while data store 212 and data store 224 may use a different data specifications that include different sets of standards and rules that define the structure, format, and/or content of data in data store 212 and/or data store 224. In some embodiments, EMR data 248 may be stored in data store 244 using a data specification that is different from the data specification used by data store 224 to store EMR data 226. The data specification used for EMR data 248 may be configured to make EMR data 248 accessible by SDM system 230, which access may include access to specific EMR data 248 in the context of specific EDC data, for example.

To this end, IDP system 240 may be configured to process ingested EMR data, including in one or more ways that prepare the EMR data for remote, on-demand access by SDM system 230. In some embodiments, the processing includes mapping EMR data 248 to clinical research source data (e.g., any data maintained by and/or ingested from CDR system 210), such as patient management data 214, EDC data 218, and data representing clinical study protocols. For example, instances of EMR data 248 may be identified as related to patients and patient visits to clinical research site 202 and mapped to patient identifiers used for the patients in clinical studies. The mappings may be determined by IDP system 240 matching information in EMR data 248 with information in CDR data 246, where CDR data 246 may represent any data maintained in CDR system 210. In some embodiments, mapping relationships between CDR data 246 and EMR data 248, which may include mapping relationships between EDC data 218 and EMR data 248, may be determined by IDP system 240 algorithmically based on one or more defined algorithms. In other embodiments, mapping relationships between CDR data 246 and EMR data 248 may be determined by IDP system 240 using one or more artificial intelligence or machine learning models that have been trained to identify mapping relationships between CDR data and EMR data. One or more matching criteria and thresholds may be defined and tuned to set confidence levels to be satisfied for an identified data relationship to be considered a data relationship for which a mapping is generated. In some implementations, this may allow EMR data that is not expressly associated with a known identifier for a clinical study patient to still be matched to the patient identifier based on other factors such as demographic information or other factors.

In some embodiments, an onboarding portal is provided and accessible to a limited set of permitted users (e.g., user roles) to manage the mappings and configurations that are used to make EMR data available to SDM system 230. In some examples, this may include defining one or more algorithms, rules, and/or inputs to algorithms and/or trained models that will be used by IDP system 240 to generate relationships between CDR data and EMR data.

In some embodiments, based on a defined configuration, IDP system 240 may support data minimization to address data privacy needs. For example, if a clinical study protocol requires information indicating whether a patient historically has had any specific illness or procedure, IDP system 240 and/or SDM system 230 may be configured to look for that specific illness or procedure in EMR data, instead of pulling EMR data for the entire medical history data of the patient.

In some embodiments, mapping operations performed by IDP system 240 may include mapping instances of EMR data to specific data fields of CDR data. For example, EDC data for a clinical study may include a data field for lab results. IDP system 240 may be configured to identify the data field, identify instances of EMR data that have relationships with lab results, and map those instances of EMR data to the data field. For instance, IDP system 240 may map, to the data field, EMR data associated with a patient visit at which a sample for lab work was collected. The EMR data may include information related to the collection of the sample and data points indicating a chain of control of the sample from its collection at the clinical research site, to its shipment to and arrival at a lab that performs the lab work, to receipt of lab results from the lab. As another example, EDC data for a clinical study may include a data field for a patient visit to a clinical research site. IDP system 240 may be configured to identify the data field, identify instances of EMR data that have relationships with the visit represented in the data field, and map those instances of EMR data to the data field. As another example, EDC data for a clinical study may include a data field for a question to be answered by a monitor as part of a monitoring workflow. IDP system 240 may be configured to identify the data field, identify instances of EMR data that have relationships with the question represented in the data field, and map those instances of EMR data to the data field.

In some embodiments, IDP system 240 may be configured to generate clinical study protocol-based mappings between CDR data and EMR data. For example, IDP system 240 may identify a protocol requirement in the CDR data, determine parameters based on the protocol requirement, and search EMR data based on the parameters. EMR data that is identified as matching (e.g., by at least a minimum confidence level) the parameters may be associated with the protocol requirement by IDP system 240 generating a mapping indicating the relationship between the protocol requirement and the identified EMR data. The mapping may be stored and configured to be used by IDP system 240 to access and provide the EMR data in the context of the protocol requirement, which protocol requirement may be part of a monitoring workflow. In some implementations, the protocol requirement may be a specific question or sub-question that is part of a monitoring workflow that is presented to a monitor during a monitoring session.

IDP system 240 may be configured to generate and maintain data representative of the mappings. The mappings data may represent any mapped relationship of CDR data to EMR data. IDP system 240 may be configured to use the mappings data to identify and provide relevant and contextual EMR data, on-demand, to SDM system 230. For example, IDP system 240 may receive a request from SDM system 230 for EMR data associated with a particular patient identifier of a patient participating in a clinical study, EMR data associated with a particular data field of EDC data associated with a particular patient identifier, EMR data associated with a particular patient visit to a particular clinical research site, EMR data associated with a monitor workflow, EMR data associated with a specific clinical study protocol requirement, EMR data associated with a specific question or sub-question of a monitoring workflow, or for EMR data related to any other specific set of criteria. IDP system 240 may use mappings data to efficiently identify and provide relevant and contextual EMR data to SDM system 230 in response to the request.

In some implementations, IDP system 240 may be configured to generate and maintain patient records for patients participating in clinical studies and to use to the patient records to maintain and/or access mappings generated by IDP system. For example, based on CDR data 246 accessed from CDR system 210, IDP system 240 may identify a patient identifier for a patient participating in a clinical study, generate a patient record associated with the patient identifier, and map the patient record to one or more instances of CDR data and/or EMR data. In some implementations, the mappings may be represented in the patient record as references (e.g., pointers) to the instances of CDR data and/or EMR data.

In some embodiments, IDP system 240 may be configured to transform EMR data from one data specification to another data specification, such as from one data format to one or more other data formats. As an example, the transformation may include standardizing the EMR data into a standard format such as United States Core Data for Interoperability (USCDI) format. In some embodiments, IDP system 240 may be configured to perform one or more data de-identification and/or filtering operations on the CDR data and EMR data.

IDP system 240 may be configured to provide an interface through which CDR data and/or EMR data is externally accessible by an authorized entity, such as a user having proper credentials to access a platform through a login process to manage a clinical research site and/or clinical research source data (e.g., by monitoring or otherwise managing one or more clinical study visits to one or more clinical research sites). In some embodiments, IDP system 240 provides an interface through which de-identified and/or filtered EMR data in USCID format is externally accessible by an authorized entity. To this end, IDP system 240 may provide a data egress interface through which SDM system 230 may access data from data store 244. In some implementations, the data egress includes an API that is accessible by authorized entities. Examples of IDP system 240 providing on-demand, controlled external access to EMR data are described herein.

Figure 3:
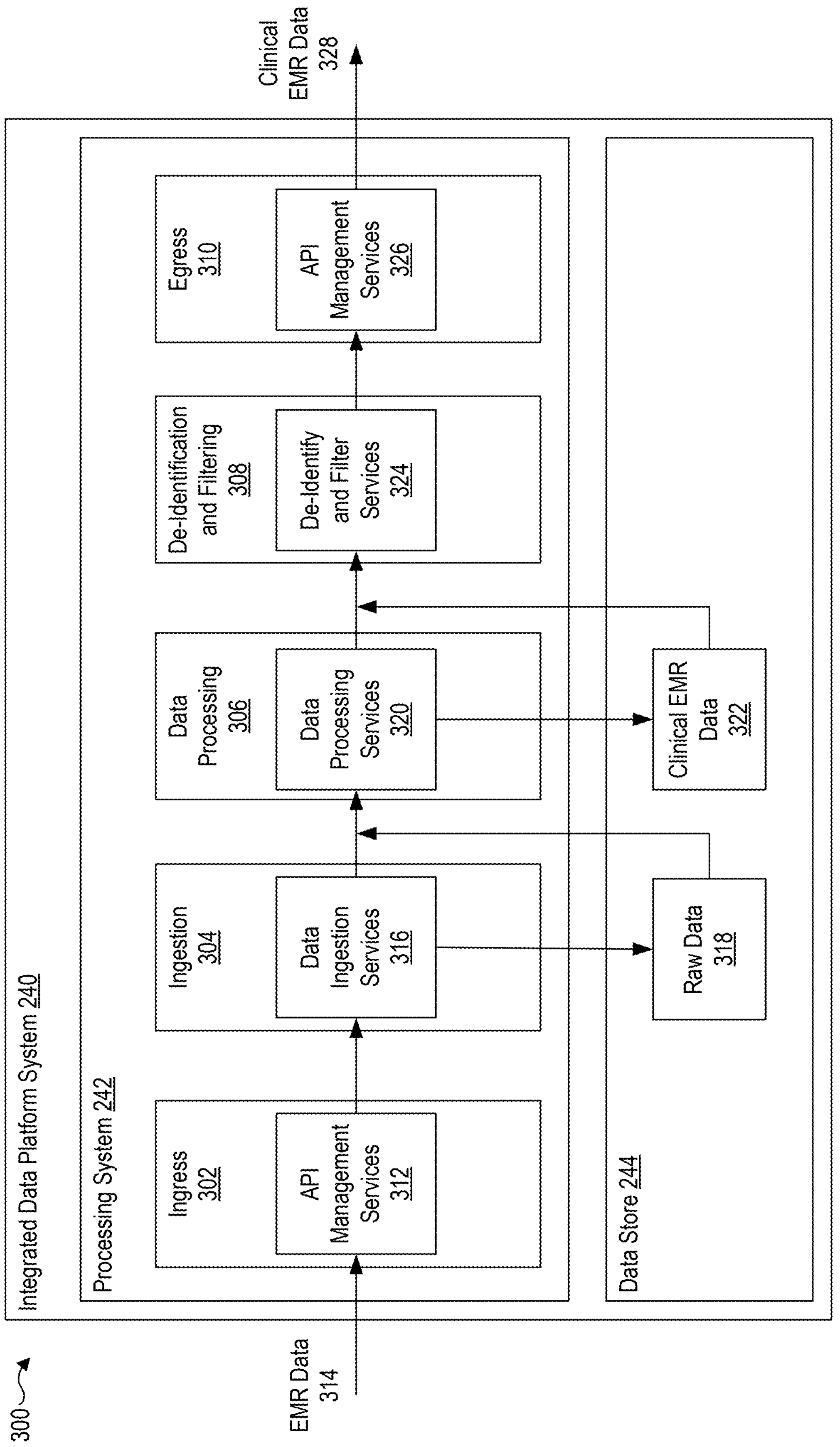
FIG. 3 illustrates an example implementation of an integrated data platform system.

FIG. 3 illustrates an example implementation 300 of IDP system 240 and an associated flow of data processing operations performed by IDP system 240 in association with EMR data. As shown, processing system 242 of IDP system 240 may include an ingress component 302, an ingestion component 304, a data processing component 306, a de-identification and filtering component 308, and an egress component 310.

Ingress component 302 may implement one or more API management services 312 configured to interact with one or more APIs of computing systems of clinical research sites such as clinical research site 202. Using API management services 312, ingress component 302 may communicate with clinical research sites to request and receive EMR data 314. IDP system 240 may be approved to access the EMR systems of the clinical research sites and provide any suitable credentials needed for the EMR systems to authorize access and fulfill requests for EMR data. As described herein, the requests may be targeted to access only EMR data that satisfies one or more request parameters, such as EMR data associated with a specific patient's visit to a specific clinical research site. Ingress component 302 may send requests and receive requested EMR data 314 from the EMR systems of clinical research sites by way of any suitable data communications technologies, including the internet, a REST interface, an HTTP interface, an API, a secure data communication link, etc. In some implementations, Ingress component 302 may send API calls to clinical research sites through an interoperability service. The API calls may be site mediated and may return EMR data, such as full or partial electronic medical records dependent on what is authorized, for consented patients associated with a site (e.g., consented patients participating in clinical research at clinical research site 202). In some implementations, a first API call to the interoperability service for a site will return EMR data for all consented patients, and subsequent API calls for the site will return only delta changes.

Ingestion component 304 may implement one or more data ingestion services 316 configured to ingest EMR data 314 into IDP system 240. The ingestion may include receiving EMR data 314 from ingress component 302 and storing the EMR data 314 in data store 244 as raw data 318. In some implementations, data ingestion services 316 may be configured to transform and validate ingested data to ensure a proper data format, such as a proper Fast Healthcare Interoperability Resources (FHIR) format in accordance with a defined FHIR standard. In some implementations, data ingestion services 316 may be configured to store ingested EMR data in a raw FHIR JSON format. Further, in some implementations, a copy of all ingested data may be stored for audit purposes. Ingestion component 304 may be configured to ingest EMR data 314 that is defined in accordance with any data specification (e.g., data format), such as data defined in accordance with the HL7 V2 data specification.

Data processing component 306 may implement one or more data processing services 320 configured to access EMR data 314 from raw data 318 at data store 244, perform one or more processes on the EMR data 314 to transform it, and store the transformed EMR data 314 as clinical EMR data 322 in data store 244. While FIG. 3 shows raw data 318 and clinical EMR data 322 stored in data store 244, raw data 318 and clinical EMR data 322 may be stored in separate data stores of IDP system 240 in other implementations. In some implementations, the transformation includes a data processing service such as a FHIR service converting EMR data from FHIR JSON format to USCDI format, normalizing the data, and storing the result, such as in a POSTgres relational database, for example. Clinical EMR data 322 may be persisted in USCDI format for case of mapping with SDM system 230.

In some embodiments, IDP system 240 is configured to collaborate with one or more interoperability vendors or services to facilitate connections to various EMR systems. Such interoperability vendors typically supply data defined in accordance with the FHIR data specification. As part of ingesting the FHIR data, the FHIR data may be transformed into the USCDI format and stored for subsequent use by other applications. IDP system 240 may be configured to consume data from multiple interoperability vendors and convert the data into the USCDI format. This allows SDM system 230 and users of SDM system 230 to remain agnostic to any changes implemented by data interoperability providers. In some embodiments, as part of the data ingestion process, numerous data points may be stored in standardized coding system formats, such as SNOMED CT, LOINC, and ICD-10/11, for example.

De-identification and filtering component 308 may implement one or more de-identification and filter services 324 configured to de-identify and filter EMR data. Such operations may be performed in advance of and/or in response to receipt of requests from SDM system 230 for EMR data. For example, in response to an API call received by egress component 310 (e.g., an API call including a request for specific patient data relevant to a clinical study and clinical research site being monitored by a clinical research monitor), requested EMR data may be determined, de-identified, and filtered based on SDM system 230 parameters (e.g., parameters that may be indicated in the API call). Any suitable data de-identification and filtering technologies may be used to perform the data de-identification and filtering processes on the EMR data. The de-identified and filtered EMR data, indicated as clinical EMR data 328 in FIG. 3, may be provided to SDM system 230 by way of egress component 310.

Egress component 310 may implement one or more API management services 326 configured to receive requests for EMR data from SDM system 230 and provide de-identified and/or filtered EMR data 328, in clinical data format, to SDM system 230. Egress component 310 may implement one or more technologies for data communications with SDM system 230. In some implementations, for example, communication between IDP system 240 and SDM system 230 may be by way of a secure communications link such as a virtual private network (VPN) tunnel with traffic routing over a backbone network. To this end, egress component 310 of IDP system 240 and SDM system 230 may each implement a VPN gateway configured to send and receive data communications over the VPN tunnel (e.g., Rest/HTTP communications).

Figure 4:
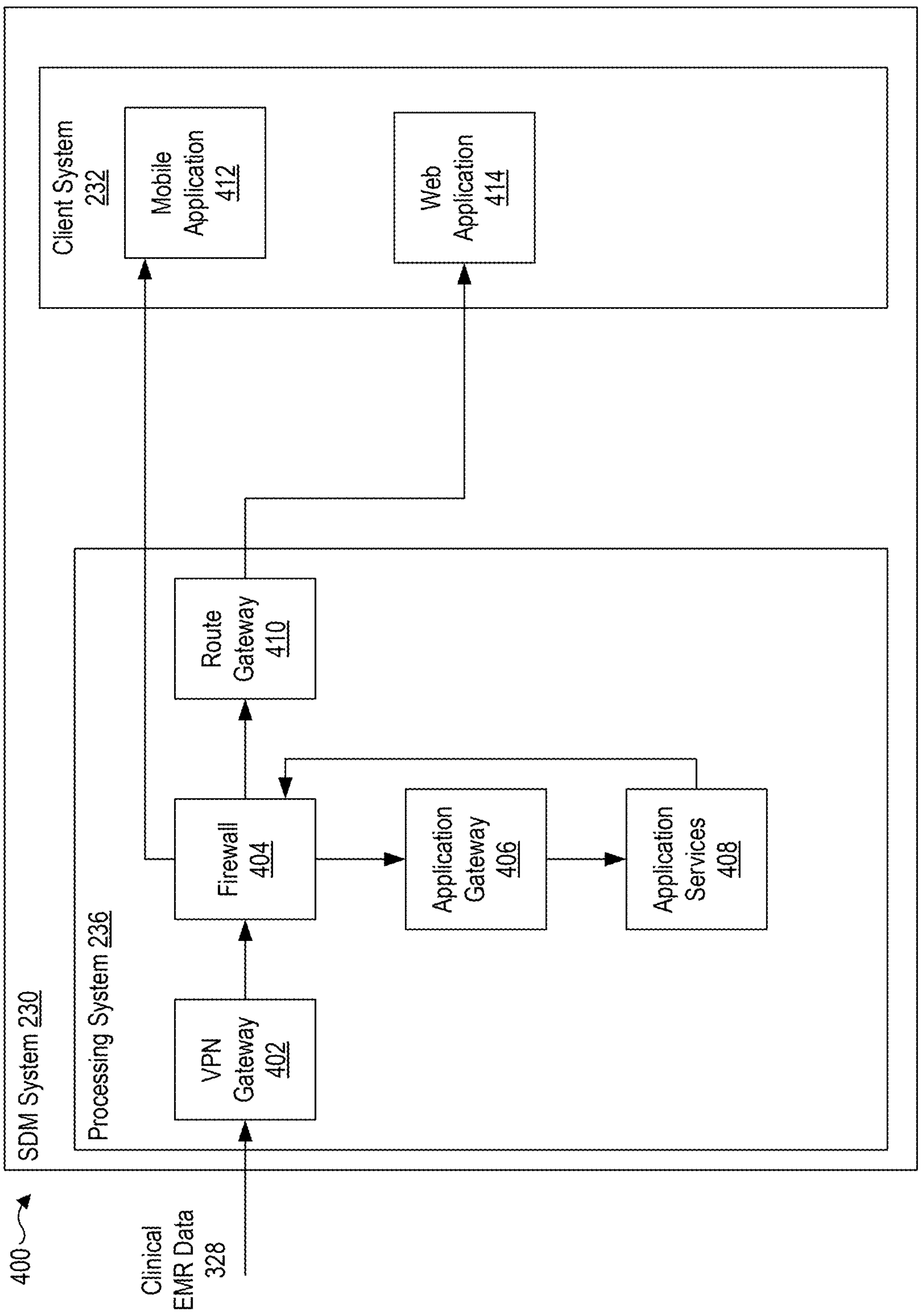
FIG. 4 illustrates an example implementation of a source data management system.

FIG. 4 illustrates an example implementation 400 of SDM system 230 and an associated flow of data processing operations performed by SDM system 230 in association with EMR data. As shown, processing system 236 of SDM system 230 may include VPN gateway 402, firewall 404, application gateway 406, application services 408, and route gateway 410. Client system 232 may include a mobile application 412 and/or a web application 414.

VPN gateway 402 receives clinical EMR data 328 from IDP system 240 and sends the EMR data to firewall 404, which may provide one or more firewall security features. Firewall 404 sends the EMR data to application gateway 406, which sends the EMR data to application services 408. Application services 408 may be configured to perform one or more application-specific data processing operations on and/or using the EMR data and send the processed EMR data and/or results to firewall 404. If the EMR data is being processed for mobile application 412 (e.g., in response to a request from mobile application), firewall 404 sends the processed EMR data to mobile application 412. If the EMR data is being processed for web application 414, firewall 404 sends the processed EMR data to route gateway 410, which sends the processed EMR data to web application 414.

In addition to the EMR data paths shown in FIG. 4, SDM system 230 may provide EDC data paths such that EDC data may be received from one or more sources (e.g., from CDR system 210 and/or IDP system 240) and provided to mobile application 412 and/or web application 414. Accordingly, EDC data and EMR data may be integrated into monitoring workflows of SDM system 230 and/or displayed together via a user interface (e.g., user interface 234) associated with mobile application 412 or web application 414. The user interface may be any user interface provided by SDM system 230 for access and presentation by mobile application 412 and/or web application 414, such as a graphical user interface having one or more graphical user interface views displaying EDC data and EMR data together (e.g., side-by-side on a single graphical user interface view or display screen).

SDM system 230 may provide one or more clinical research monitoring workflows for use by a user (a clinical research monitor such as a CRA) of client system 232 to review clinical research source data and/or clinical research sites while the user is offsite, remote from the clinical research sites. The workflows may be predefined and/or may be defined in real time or near real time based on clinical study protocols and/or any other clinical research monitoring requirements.

As an example, SDM system 230 may provide a workflow for use by a user to monitor a clinical study and patient visits to clinical research sites conducting the clinical study. The workflow may be configured to guide the user to perform monitoring activities, including performing reviews of data and providing user input indicative of the user's findings.

The workflow may be configured to integrate EDC data and EMR data accessed by SDM system 230. The integrations of EDC data and EMR data into the workflows provide one or more practical applications of the data and the data platforms (e.g., IDP 240) that deliver the data to SDM system 230 as described herein.

SDM system 230 may be configured to provide the workflow via a user interface such as user interface 234. For example, the workflow may be associated with an organized structure and flow of graphical user interface views by way of which the EDC data and EMR data are presented, as well as one or more review tools configured to be interacted with by the user to provide user input related to the user's review of the data and/or events related to collection of the data. The review tools may be provided via the user interface and in association with EDC data and EMR data, as part of the workflow.

The review tools may include any user interface tools usable by the user to access and review EDC data and EMR data (including EDC data and EMR data displayed together such as side-by-side in a single graphical user interface view), access and review specific EMR data that is contextually related to specific EDC data, annotate EDC data with one or more annotations, indicate whether process execution associated with collection of EDC data was compliant or non-compliant (e.g., whether the patient or the clinical research site was non-compliant), create a record of a protocol deviation (e.g., flag specific EDC data as being associated with a protocol deviation and provide a description of the deviation), create a record of an adverse interaction or event (e.g., flag specific EDC data as being associated with an adverse event and provide a description of the event), initiate a source data verification (SDV) process to compare EDC data to EMR data (e.g., by comparing clinical research data to original source documents to check for accuracy and reliability), initiate a source data review (SDR) process to review EMR data (e.g., original source documents represented in the EMR data), mark EDC data as validated or not validated, indicate that no EMR data is available to use to review EDC data and/or to answer a workflow question, create a query and annotate EDC data with the query, send a notification of the query to a clinical study investigator, monitor, or sponsor, create digital notes and annotate EDC data and/or the workflow data with the notes, access one or more questions and sub-questions of the workflow, provide answers to the questions and sub-questions, access and review specific and contextually relevant EMR data in the context of a workflow question or sub-question, update EDC data in a clinical data repository such as data store 212 of CDR system 210, select a workflow or EDC data category or data field (e.g., an eCRF data field) for display, and to perform any other clinical trial review activities as part of the workflow. In some implementations, one or more of the above monitoring activities may be configured, within the workflow, to trigger presentation of specific and contextually relevant EMR data in the context of the monitoring activities.

FIGS. 5-12 illustrate example graphical user interface views that may be provided by SDM system 230 as part of one or more clinical research monitoring workflows. One or more of the graphical user interface include review tools, such as data presentation panes and user-selectable options, configured to be used by a user to review EDC data and contextually relevant EMR data and provide input and/or perform other actions based on the review of the data.

Figure 5:
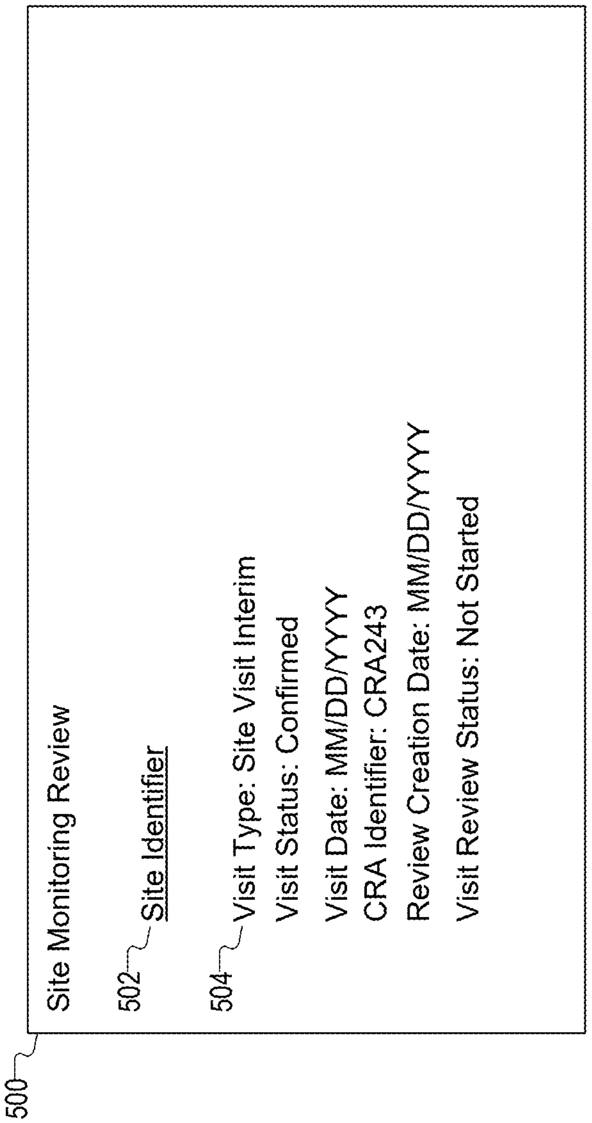
FIG. 5 illustrates an example graphical user interface view.

FIG. 5 illustrates an example view 500 for a site monitoring review. As shown, view 500 includes a site identifier 502 for a clinical research site and information 504 related to a review of the site. Information 504 may indicate values for a visit type, a visit status, a visit date, a review creation date, a visit review status, and any other information related to a review of the site.

Site identifier 502 and information 504 may include or be derived from EDC data accessed by SDM system 230. For example, EDC data may be accessed in response to user input to user interface 234 and/or as part of generating view 500 for display. Site identifier 502 may comprise a selectable link to access more information and options related to the review of the site.

Figure 6:
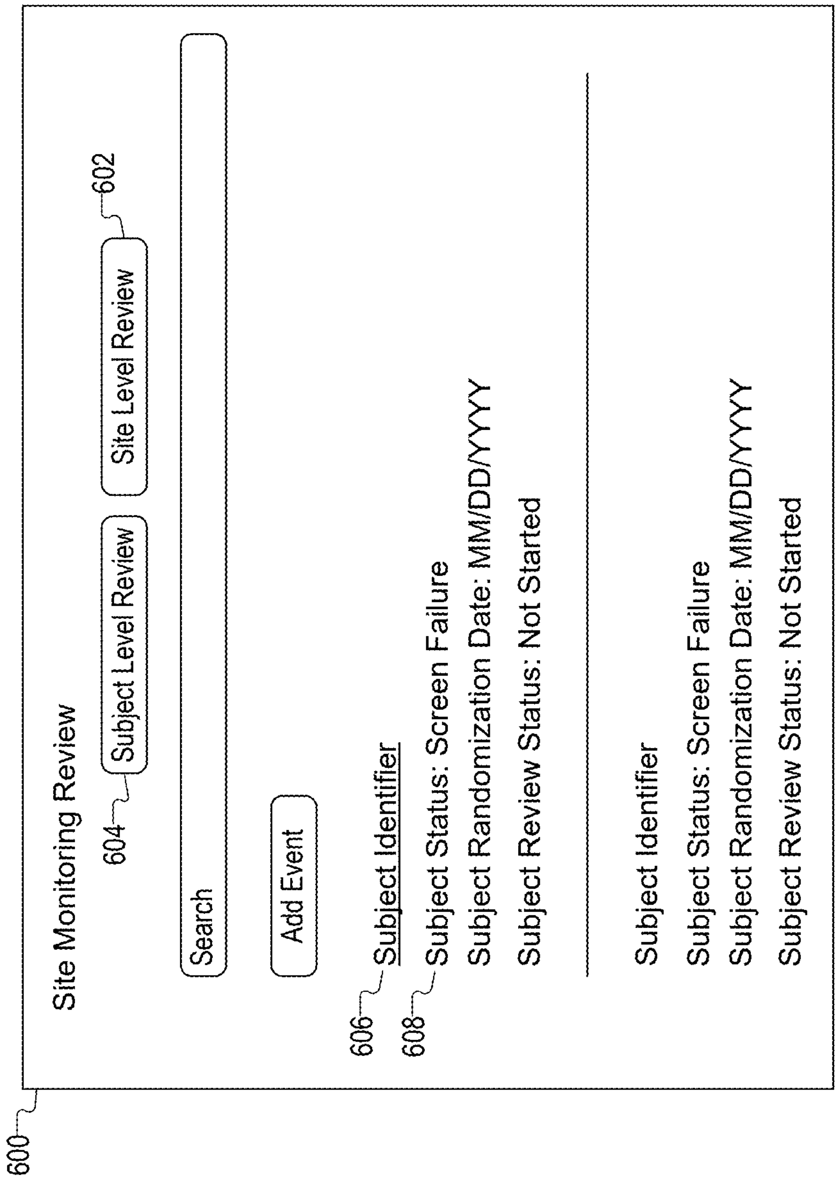
FIG. 6 illustrates another example graphical user interface view.

FIG. 6 illustrates an example view 600 for a subject level review that is part of a site monitoring review workflow. As shown, view 600 includes a user-selectable site level review option 602 and a user-selectable subject level review option 604. Option 604 has been selected to trigger display of a list of information about subjects (i.e., patients) participating in a clinical research study as the clinical research site being reviewed. As shown, the list includes a first entry indicating a subject identifier 606 for a subject and information 608 about the subject. Information 608 may indicate values for a subject status, a subject randomization date, a subject review status, and any other information related to the subject.

Subject identifier 606 and information 608 may include or be derived from EDC data accessed by SDM system 230.

For example, EDC data may be accessed in response to user input to user interface 234 and/or as part of generating view 600 for display. Subject identifier 606 may comprise a selectable link to access more information and options related to the review of the subject.

Figure 7:
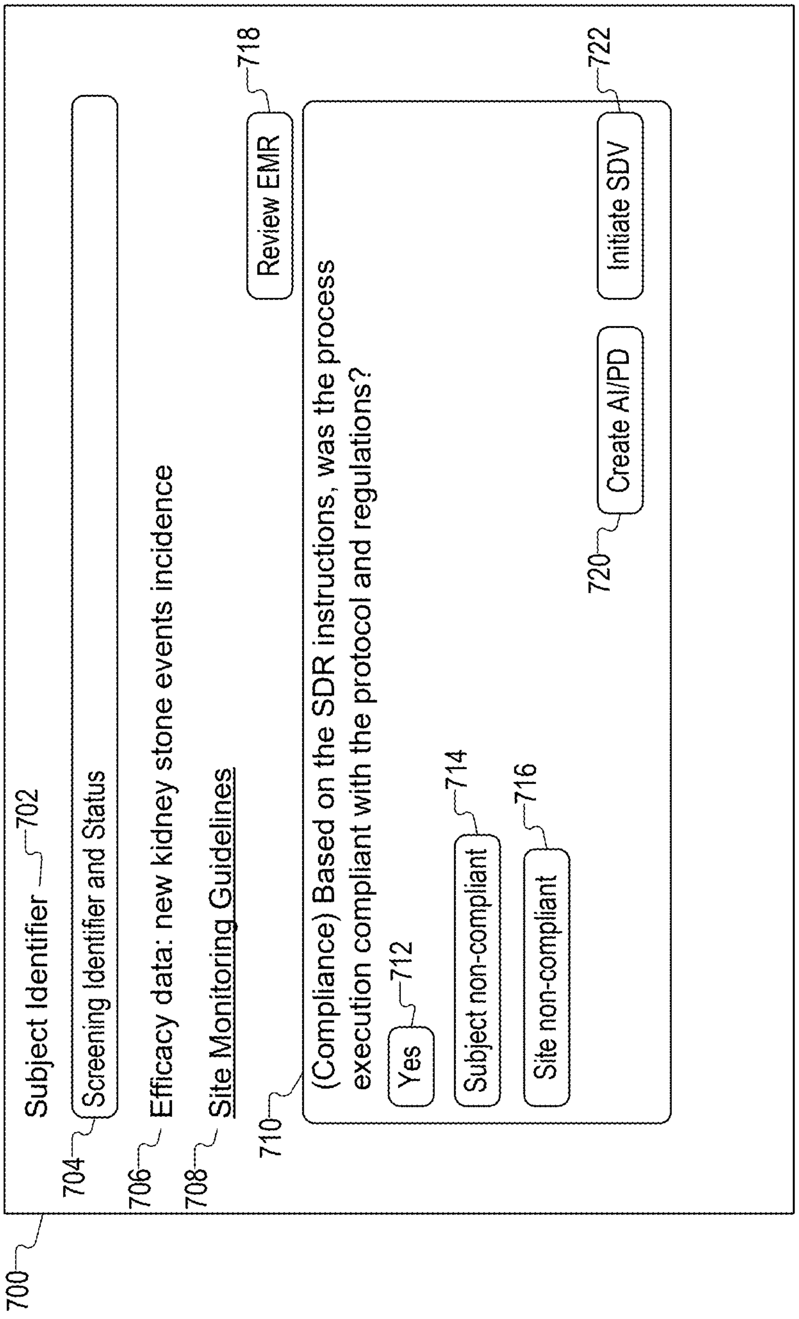
FIG. 7 illustrates another example graphical user interface view.

FIG. 7 illustrates an example view 700 for a subject screening that is part of a site monitoring review workflow. As shown, view 700 includes a subject identifier 702 for a selected subject and a user-selectable screening identifier and status option 704 that has been selected to launch the information and user-selectable options shown below it. View 700 further includes a visit or event description 706 and a link 708 to site monitoring guidelines.

View 700 includes a screening pane 710 in which a compliance-related workflow question is displayed. Screening pane 710 further includes user-selectable options each selectable by the user to indicate an answer to the question. Option 712 may be selected to indicate compliance, option 714 may be selected to indicate subject non-compliance, and object 716 may be selected to indicate site non-compliance.

To assist the user in answering the question, view 700 includes a user-selectable option 718 to access and review EMR data that is related to the question. Examples of views that may be displayed in response to a user selection of option 718 are described herein.

View 700 further includes a user-selectable option 720 to create a record of a protocol deviation (PD) or adverse interaction (AI) or event. View 700 also includes a user-selectable option 722 to initiate a source data verification (SDV) process, which may be part of the workflow.

Information and/or options included in view 700 may include or be derived from EDC data accessed by SDM system 230. For example, EDC data may be accessed in response to user input to user interface 234 and/or as part of generating view 700 for display. User selection of any of options 712, 714, 716, and 720 may cause SDM system 230 to annotate EDC data to reflect review feedback, such as by sending data representative of an annotation to CDR system 210 for addition to data store 212 (e.g., as an annotation to EDC data 218 and/or review data).

Figure 8:
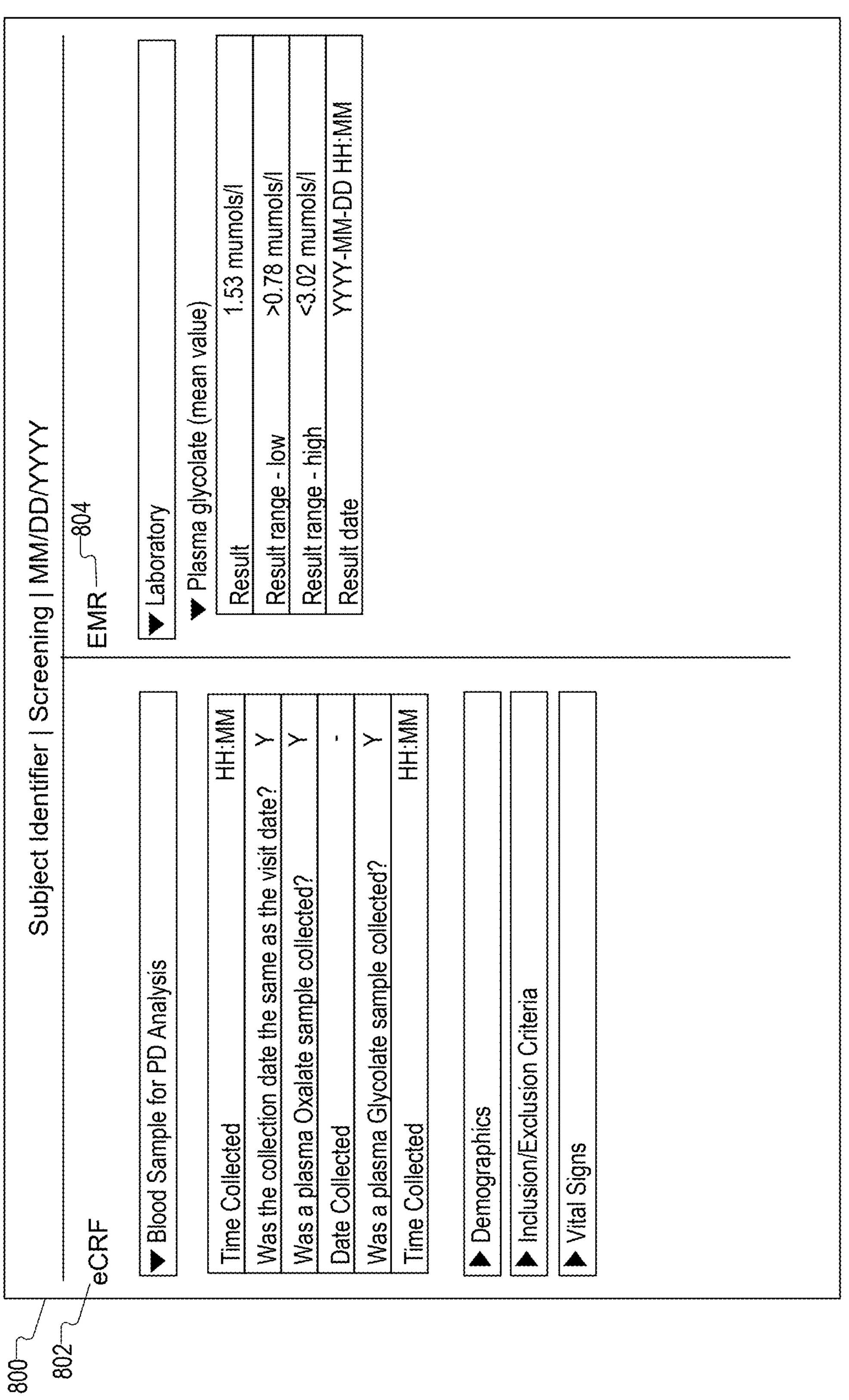
FIG. 8 illustrates another example graphical user interface view.

FIG. 8 illustrates an example view 800 for a subject screening review that is part of a site monitoring review workflow. As shown, view 800 includes a first pane 802 in which EDC data-based information and options are presented. The content of pane 802 may include information and options corresponding to eCRF data categories. In the illustrated example, the options correspond to eCRF data categories of blood sample for protocol deviation (PD) analysis, demographics, inclusion/exclusion criteria, and vital signs. The option for the blood sample for PD analysis has been selected for expansion to present data fields within the data category and values for those data fields. In the illustrated example, the data fields include a time collected field, a sub-question asking whether the collection date was the same as the visit date, a sub-question asking whether a plasma oxalate sample was collected, a data collected field, a sub-question asking whether a plasma glycolate sample was collected, and a time collected field, as well as known values for the fields/questions.

View 800 further includes a second pane 804, displayed together with and adjacent (e.g., side-by-side) to first pane 802, in which EMR data-based information and options are presented. The content of pane 804 may include information and options that are contextually relevant to the content of first pane 802. In the illustrated example, an option corresponding to an EMR data category of laboratory has been selected for expansion and includes information about lab results for lab work done for a plasma glycolate sample.

EMR data for the relevant laboratory lab work may be identified and displayed in pane 804 in response to any event, including, for example, display of EDC data in pane 802. The relevant EMR data may be identified based on one or more mappings of the EMR data to EDC data displayed in first pane 802. By displaying contextually relevant EMR data together with EDC data in view 800, the user may perform monitoring activities using EMR data to review EDC data and collection events for the EDC data efficiently even when offsite from the clinical research site being monitored.

Figure 9:
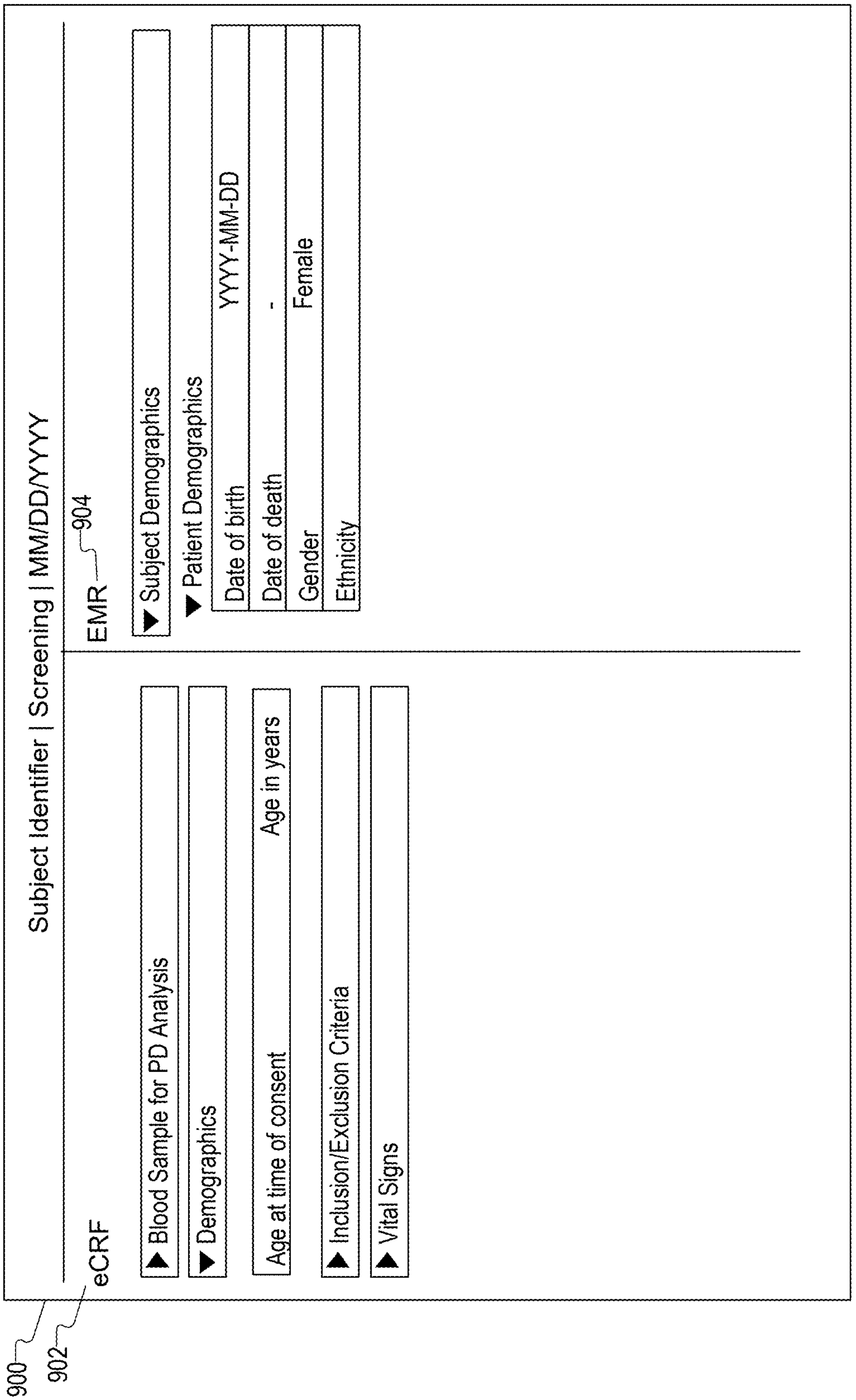
FIG. 9 illustrates another example graphical user interface view.

FIG. 9 illustrates an example view 900 for a subject screening review that is part of a site monitoring review workflow. As shown, view 900 includes a first pane 902 and second pane 904, as in FIG. 8. In pane 902, however, a different EDC data-based category, demographics, has been selected for expansion to present data fields within that data category and values for those data fields. In the illustrated example, the data fields include an age-at-time-of-consent data field and a value for the field. In pane 904, different EMR data-based information and options relevant to the content of first pane 902 are displayed. In the illustrated example, an option corresponding to an EMR data category of subject demographics has been selected for expansion and includes information about patient demographics.

EMR data for the relevant patient demographics may be identified and displayed in pane 904 in response to any event, including, for example, user selection of the EDC data-based category named demographics in first pane 902 and/or display of EDC data for subject demographics in pane 902. The relevant EMR data may be identified based on one or more mappings of the EMR data to EDC data displayed in first pane 902. By displaying contextually relevant EMR data together with EDC data in view 900, the user may perform monitoring activities using EMR data efficiently even when offsite from the clinical research site being monitored.

Figure 10:
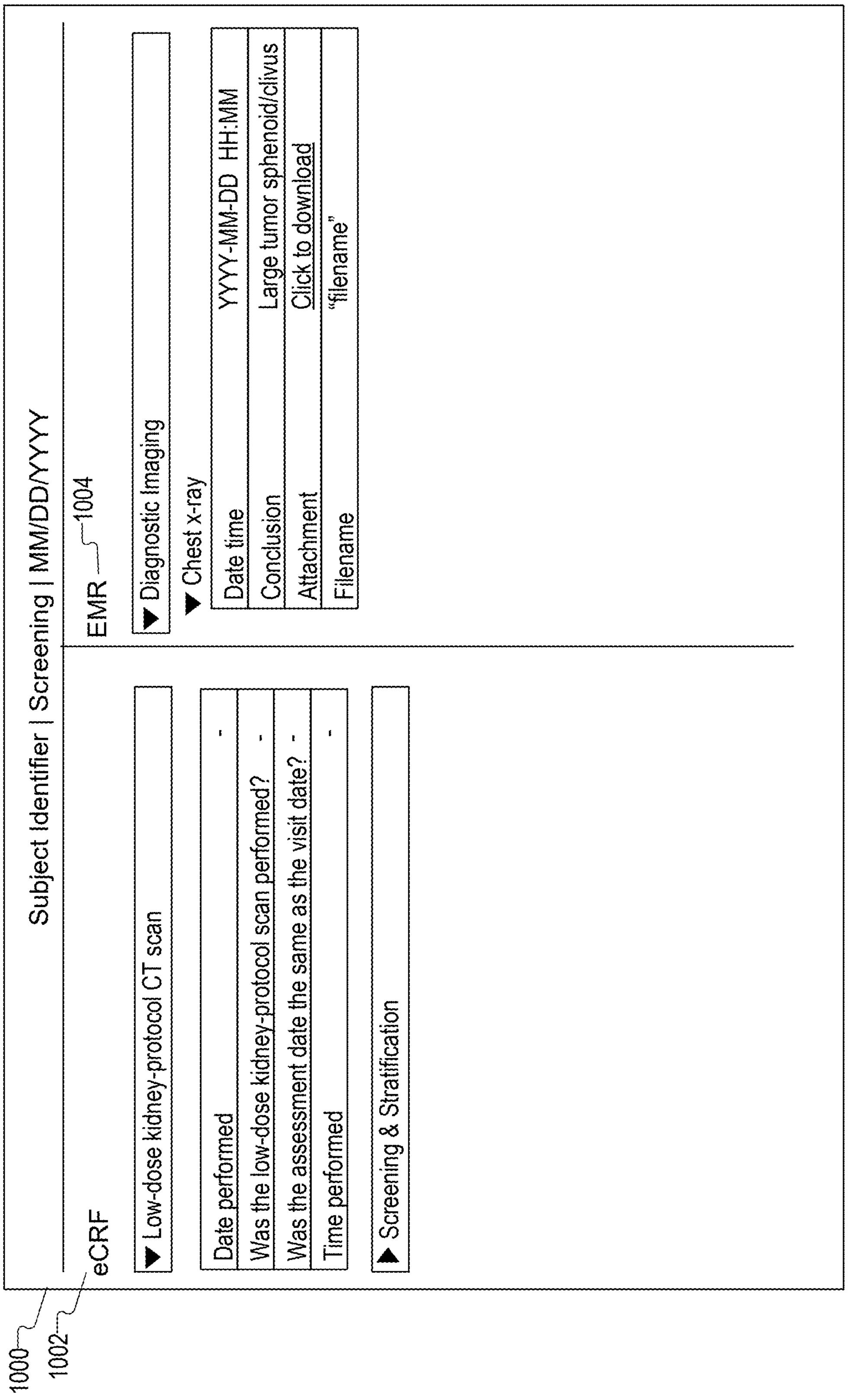
FIG. 10 illustrates another example graphical user interface view.

FIG. 10 illustrates an example view 1000 for a subject screening review that is part of a site monitoring review workflow. As shown, view 1000 includes a first pane 1002 and second pane 1004, as in FIG. 9. In pane 1002, however, a different EDC data-based category, low-dose kidney-protocol CT scan, has been selected for expansion to present data fields within that data category. In the illustrated example, the data fields include a date performed field, a question asking whether the low-dose kidney-protocol scan was performed, a question asking whether the assessment date was the same as the visit data, and a time performed field. In pane 904, different EMR data-based information and options relevant to the content of first pane 902 are displayed. In the illustrated example, an option corresponding to an EMR data category of diagnostic imaging has been selected for expansion and includes information about a patient's chest x-ray.

EMR data for the relevant diagnostic imaging may be identified and displayed in pane 904 in response to any event, including, for example, user selection of the EDC data-based category named low-dose kidney-protocol CT scan in first pane 902 and/or display of EDC data for an imaging scan in pane 902. The relevant EMR data may be identified based on one or more mappings of the EMR data to EDC data displayed in first pane 1002. By displaying contextually relevant EMR data together with EDC data in view 1000, the user may perform monitoring activities using EMR data efficiently even when offsite from the clinical research site being monitored.

Figure 11:
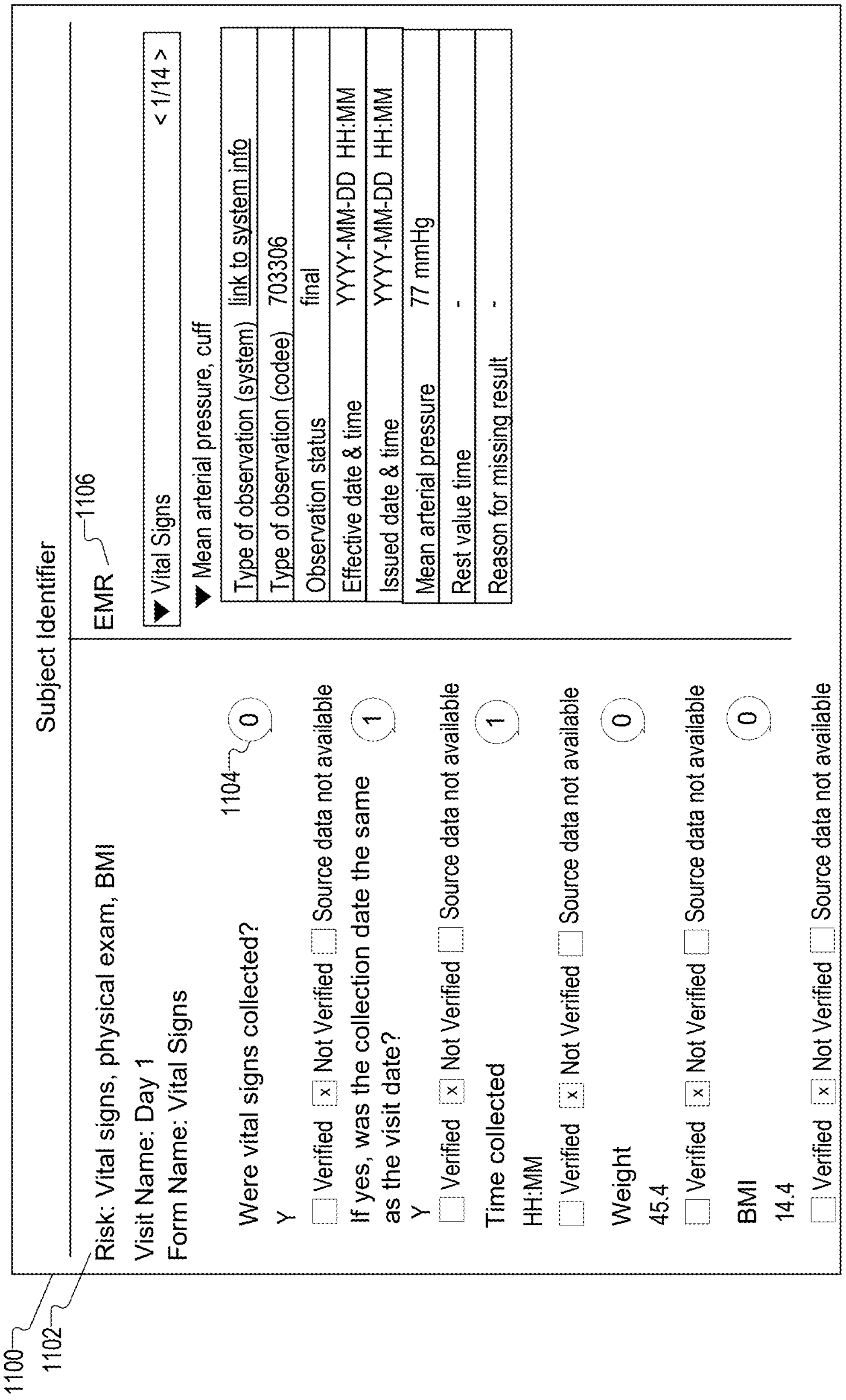
FIG. 11 illustrates another example graphical user interface view.

FIG. 11 illustrates an example view 1100 for a subject screening review that is part of a site monitoring review workflow. As shown, view 1100 includes first pane 1102 in which EDC data-based content is presented. The content of pane 1102 may include information, questions, answers, and review options corresponding to eCRF data categories for a form named "Vital Signs." In the illustrated example, the content includes a question asking whether vital signs were collected, an affirmative answer ("Y") to the question, and options indicating whether the collection of the vital signs has been verified, has not been verified, or does not have source data available for verification. In some embodiments, these options may be user-selected such that the user may change the verification status of the question and/or EDC data associated with the question. The content of first pane 1102 further includes additional content fields, including a question asking whether the date of collection of the vital signs is the same as the visit date, a time collected field, a weight field and a BMI field, as well as values for these questions and fields.

For each EDC data field represented in pane 1102, pane 1102 includes a comment indicator, such as comment indicator 1104 indicating a number of comments (e.g., annotations, natural language notes, queries, etc.) that are associated with the data field in the EDC data and/or review data. For example, comment indicator 1104 indicates there are no comments in the EDC data that are associated with the question asking whether vital signs were collected. In some implementations, the comment indicator 1104 indicates the number of queries raised for the corresponding data points. A query may be raised by a user of SDM system 230, such as a clinical research monitor, via a user interface provided by SDM system 230. A query, for example, may be created if there are ambiguities or anomalies in the reviewed data. In response to user input creating a query for a data point, SDM system 230 may communicate with CDR system 210 to record the query on the data point in the CDR system 210, such as in an EDC system.

View 1100 further includes a second pane 1106, displayed together with and adjacent (e.g., side-by-side) to first pane 1102, in which EMR data-based information and options are presented. The content of pane 1106 may include information and options that are contextually relevant to the content of first pane 1102. In the illustrated example, an option corresponding to an EMR data category of vital signs has been selected for expansion and includes information about the collected vital signs and the collection of the vital signs, as represented in EMR data.

EMR data for the relevant vital signs may be identified and displayed in pane 1106 in response to any event, including, for example, display of EDC data, in pane 1102, that has been mapped, as described above, to specific EMR data for the relevant collection of vital signs. By displaying contextually relevant EMR data together with EDC data in view 1100, the user may perform monitoring activities using EMR data efficiently even when offsite from the clinical research site being monitored.

Figure 12:
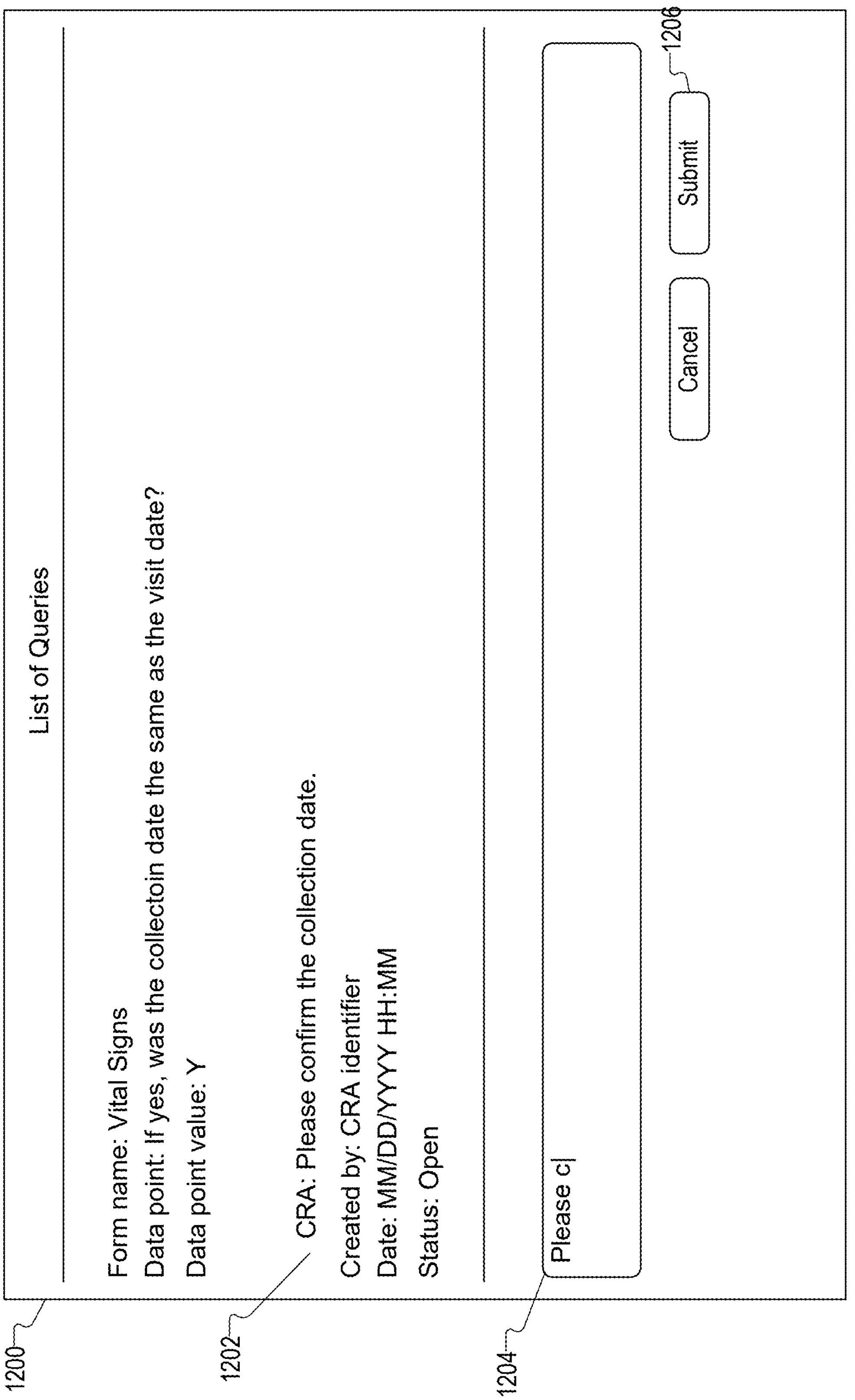
FIG. 12 illustrates another example graphical user interface view.

FIG. 12 illustrates an example view 1200 for query management that is part of a site monitoring review workflow. As shown, view 1200 includes query information 1202 mapped to an eCRF form named "Vital Signs." The query information 1202 represents a query that has been submitted by a user, identified as "CRA identifier," and includes a request that the collection date be confirmed. The query may be sent by SDM system 230 to an investigator, monitor, and/or sponsor associated with a clinical study.

View 1200 further includes tools for use by a user to create and submit a new query, such as by entering a text query in a text box 1204 and selecting a submit option 1206 to submit the query to the SDM system 430.

As part of monitoring workflows provided by SDM system 230, including as part of a monitoring workflow associated with one or more of the graphical user interface views shown in FIGS. 5-12, SDM system 230 may be configure to generate notifications such as alerts based on user input and/or detection of protocol deviations, adverse events, data discrepancies, or any other issue with EDC data or the collection of EDC data. For example, a notification such as an alert may be generated and sent by SDM system 230 to an investigator, monitor, and/or sponsor associated with a clinical study. In some examples, SDM system 230 may be configured to provide a notification by annotating data in CDR system 210, e.g., EDC data 218, with data representative of the notification.

SDM system 230 may be configured to employ one or more safeguards to protect and control access to data that is accessed, used, and presented by SDM system 230. In particular, SDM system 230 may be configured to safeguard EDC data and/or EMR data used by SDM system 230. For example, SDM system 230 may be configured to prevent persistence of the EDC data and/or EMR data retrieved by SDM system 230 such that persistence of the EDC data and/or EMR data is prevented within SDM system 230 (e.g., within processing system 236 and/or client system 232). Accordingly, SDM system 230 may access and present EDC data and EMR data for review by a user, while also preventing that data from being persisted in the computing domain of SDM system 230. This not only protects the data, it also allows SDM system 230 to retrieve and use data at high data rates/speeds.

In some embodiments, persistence of data may be prevented to address data privacy requirements. For example, a component of SDM system 240, such as a mobile application, may make API calls during a user session to retrieve EMR data and EDC data in real time or near real time and display the data in a user interface of SDM system 240. The data may be accessible only for the duration of the active session. When the session ends, such as when the user logs out or the session expires due to inactivity, the data is removed from the mobile application and/or SDM system 240 without being persisted. Additionally, the mobile application may be configured to prevent the user of the mobile application and/or the device on which the mobile application is running from taking screenshots or sharing the screen while the mobile application is running in the foreground.

SDM system 230 may be configured to employ one or more additional safeguards, such as by controlling access to the data by authorized entities, systems, devices, and personnel. For example, a user attempting to access SDM system 230 is required to present proper credentials, such as through a login process to manage one or more clinical study visits to one or more clinical research sites. SDM system 230 is configured to grant access only when proper credentials are received and validated. SDM system 230 may limit an authenticated and authorized user's access to only data that the user is permitted to access. In addition, SDM system 230 may access only de-identified and filtered EMR data in some examples. SDM system 230 may also employ data encryption technologies to decrypt retrieved data and encrypt data for transmission via secure communication links.

Figure 13:
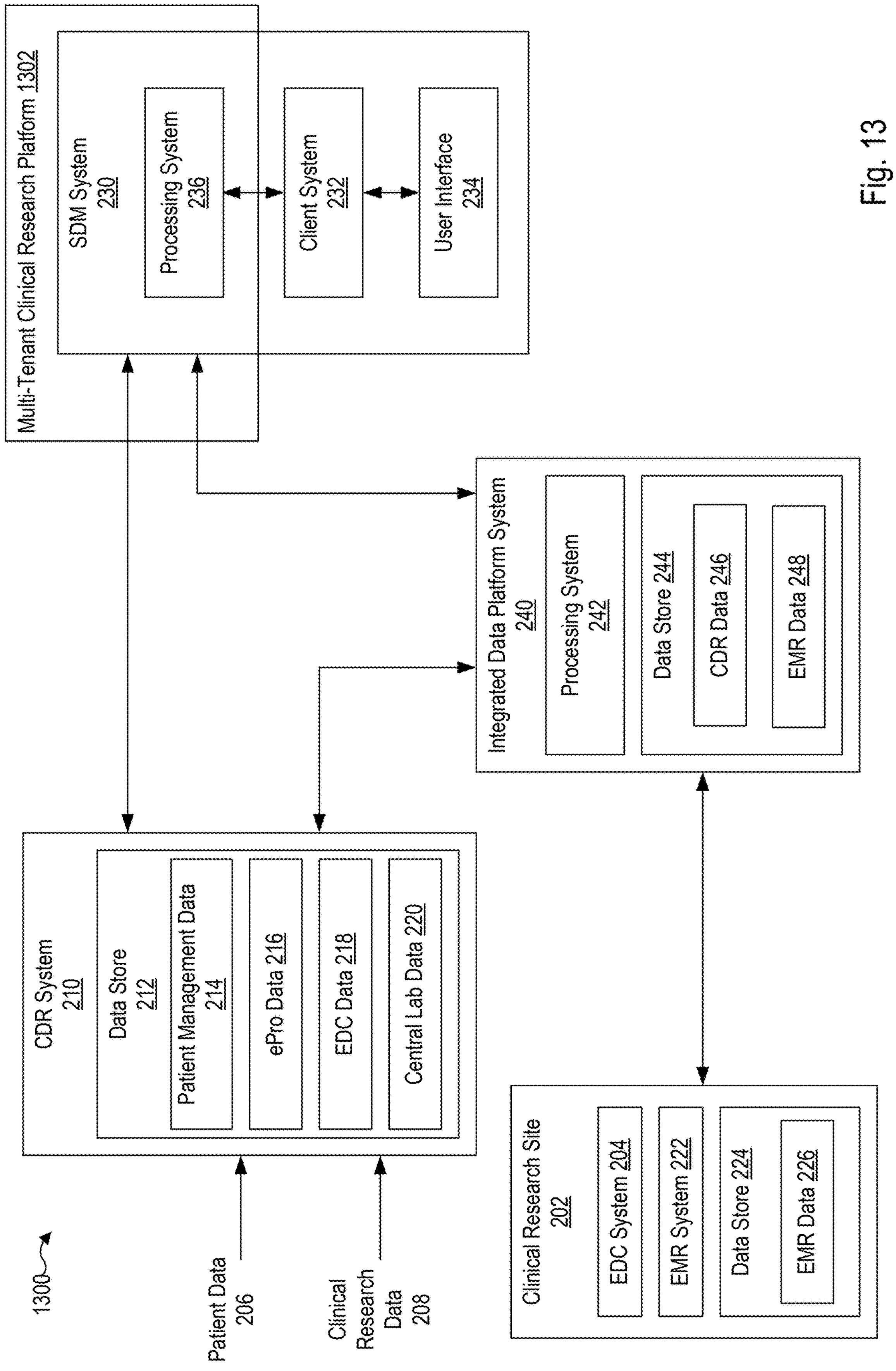
FIG. 13 illustrates an example configuration that uses a multi-tenant clinical research platform for remote management of clinical research source data and/or clinical research sites.

One or more components of system 200 of FIG. 2 may be configured to implement a multi-tenant clinical research platform for remote management of clinical research source data and/or sites. For example, FIG. 13 illustrates a system 1300 that is system 200 with processing system 236 of SDM system 230 configured to function as a multi-tenant clinical research platform (CRP) 1302 for remote management of clinical research source data and/or sites. CRP 1302 may perform any of the operations of SDM system 230 described herein, including communicating with one or more CDR systems such as CDR system 210, IDP system 240, and one or more client systems such as client system 232, as well as other operations described herein in reference to CRP 1302.

In alternative embodiments, a multi-tenant CRP for remote management of clinical research source data and/or sites may be configured to include additional components of system 200. For example, a multi-tenant CRP may include processing system 236 of SDM system 230 and IDP system 240 configured to function as the multi-tenant CRP. As another example, a multi-tenant CRP may include processing system 236 of SDM system 230, IDP system 240, and CDR system 210 configured to function as the multi-tenant CRP.

A CRP such as CRP 1302 may be configured to access an EDC data store containing EDC data for a plurality of digitized clinical studies each having a set of clinical study protocols. For example, CRP 1302 may be configured to access data store 212 of CDR system 210 and/or data store 244 of IDP system 240. CRP 1302 may be further configured to access an EMR data store containing EMR data about a plurality of patients. For example, CRP 1302 may be configured to access data store 244 of IDP system 240. CRP 1302 may be further configured to access and use mappings between EDC data for one or more clinical study visits and EMR data associated with the clinical study visits, such as any of the mappings described herein, in order to access EMR data that is relevant to the context of specific EDC data.

CRP 1302 may be configured to access/generate and maintain patient records representative of patients participating in clinical studies and to use the patient records to maintain and/or access mappings generated by IDP system 240. The patient records may be based on clinical research source data maintained by CDR system 210 and/or patient data maintained by IDP system 204. For example, based on clinical research source data maintained by CDR system 210, CRP 1302 may identify a patient identifier for a patient participating in a clinical study, generate a patient record associated with the patient identifier, and map the patient record to data store 212 by including a reference (e.g., a pointer) to data store 212 in the patient record. CRP 1302 may also map the patient record to IDP system 240, such as to data store 244, by including a second reference (e.g., a second pointer) to data store 244 in the patient record. Accordingly, when CRP 1302 receives a request to access the patient record for a patient (e.g., for a patient's clinical study visit to a clinical research site), CRP 1302 may retrieve and use the patient record to access EDC data for the patient (e.g., for the patient's clinical study visit to the clinical research site) and EMR data associated with the patient (e.g., associated with the patient's clinical study visit to the clinical research site). The EMR data may be retrieved based on mappings between the EDC data and the EMR data that have been generated by IDP system 240 and may be accessed and used by CRP 1302.

Figure 14:
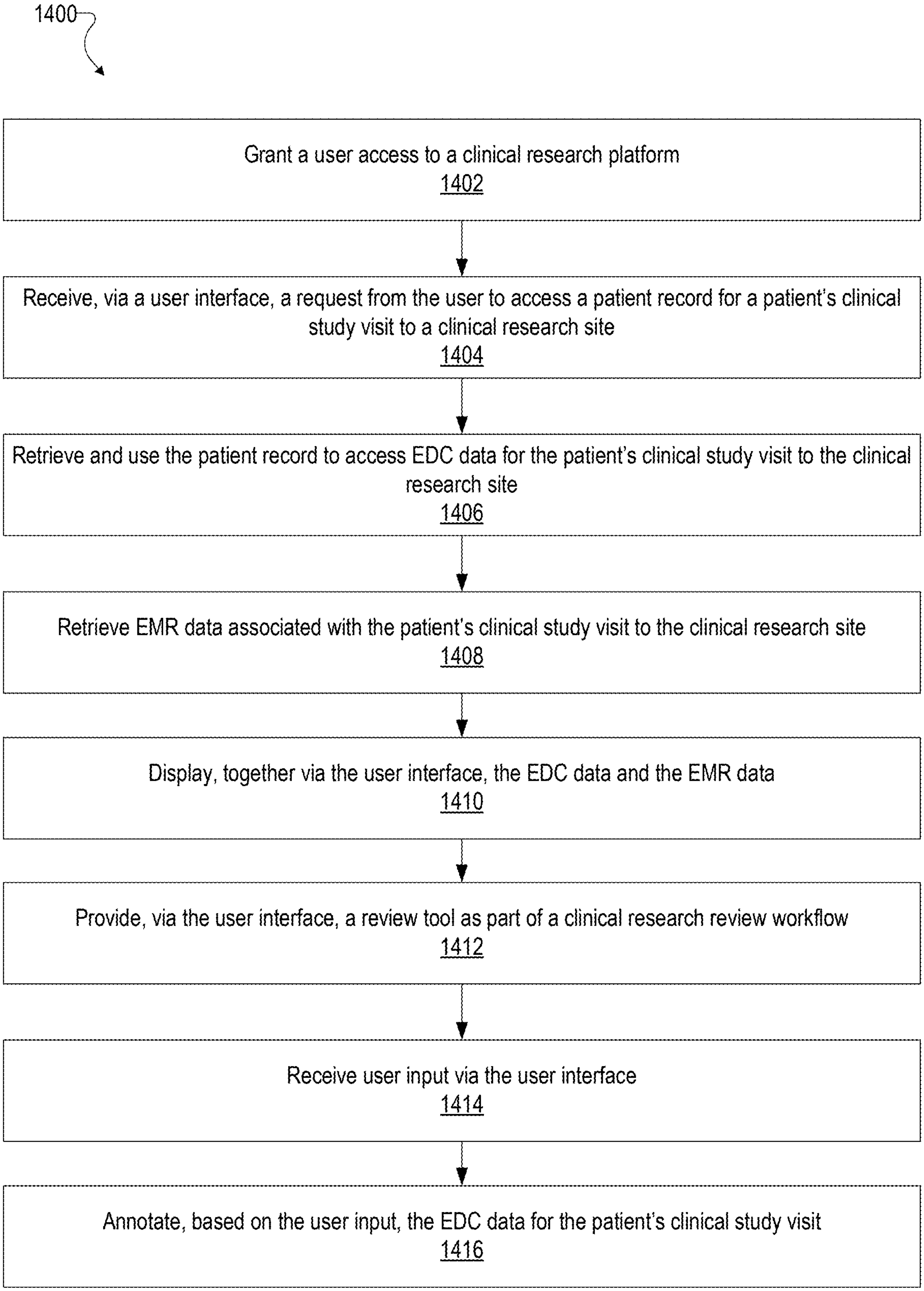
FIG. 14 illustrates an example method for remote management of clinical research.

FIG. 14 shows an illustrative method 1400 of remote management of clinical research. Any of the computing systems described herein may perform method 1400. For example, method 1400 may be performed by a clinical research platform such as CRP 1302. While FIG. 14 shows illustrative operations of method 1400, one or more operations may be combined, reordered, omitted, or added in other embodiments. The operations may be performed in any of the ways described herein.

At operation 1402, a clinical research platform grants a user access to the clinical research platform. For example, the platform may grant the user access to the platform through a login process to manage one or more clinical study visits to one or more clinical research sites. As described herein, the platform may be configured to access, via a first network connection, an EDC data store containing EDC data for a plurality of digitized clinical studies each having a set of clinical study protocols. The platform may be further configured to access, via a second network connection, an EMR data store containing EMR data about a plurality of patients. As described herein, the EMR data store and the EDC data store are separate from one another and implement different data specifications, and the platform is further configured to access and use mappings between EDC data for the clinical study visits and EMR data associated with the clinical study visits to access request and retrieve EMR data that is contextually relevant to specific EDC data.

At operation 1404, the clinical research platform receives, via a user interface, a request from the user to access a patient record for a patient's clinical study visit to a clinical research site.

At operation 1406, the clinical research platform retrieves and uses the patient record to access EDC data for the patient's clinical study visit to the clinical research site.

At operation 1408, the clinical research platform retrieves EMR data associated with the patient's clinical study visit to the clinical research site.

At operation 1410, the clinical research platform displays, together via the user interface, the EDC data and the EMR data.

At operation 1412, the clinical research platform provides, via the user interface, a review tool as part of a clinical research review workflow. The review tool may include any of the illustrative monitoring tools and/or graphical user interface features (e.g., data presentation configurations and/or user-selectable options) described herein.

At operation 1414, the clinical research platform receives user input via the user interface. For example, the user input may be received via the review tool, such as based on user interaction with the review tool.

At operation 1416, the clinical research platform annotates, based on the user input, the EDC data for the patient's clinical study visit. The platform may annotate the EDC data in any suitable way, such as by sending, to CDR system 210, data representative of an update to be made to CDR data maintained by CDR system 210. CDR system 210 may receive and application the update to CDR data. The annotation may be made in any suitable way, such as by annotating EDC data or other data in CDR system 210. The annotation may be based on and/or indicate user feedback provided by a user of SDM system 230 regarding EDC data and/or the collection of EDC data, such as whether the EDC data or its collection was compliant or not compliant with study protocols, whether EDC data or its collection is verified or not verified, that a data discrepancy exists, a query to be presented to an investigator, monitor, or sponsor a clinical study, a remediation recommendation such as an action to be performed by an investigator, monitor, or sponsor of a clinical study, a protocol deviation associated with collection of EDC data, an adverse event associated with collection of EDC data, and/or any other annotation related to review of EDC data and its collection.

Figure 15:
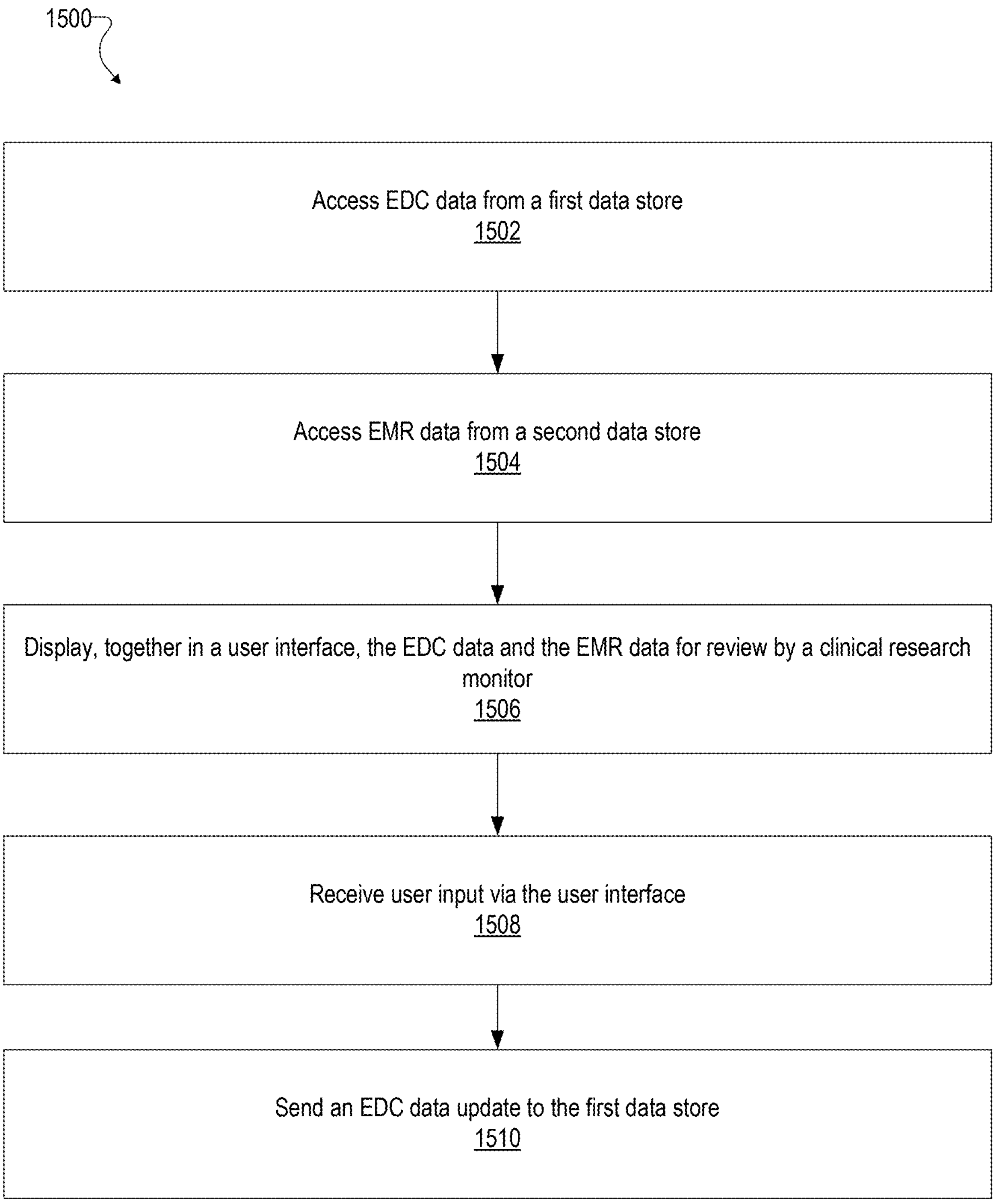
FIG. 15 illustrates an example method for remote management of clinical research.

FIG. 15 shows an illustrative method 1500 of remote management of clinical research. Any of the computing systems described herein may perform method 1500. For example, method 1500 may be performed by a clinical research platform such as CRP 1302. While FIG. 15 shows illustrative operations of method 1500, one or more operations may be combined, reordered, omitted, or added in other embodiments. The operations may be performed in any of the ways described herein.

At operation 1502, a clinical research platform accesses EDC data from a first data store.

At operation 1504, the clinical research platform accesses EMR data from a second data store.

At operation 1506, the clinical research platform displays, together in a user interface, the EDC data and the EMR data for review by a clinical research monitor. The display of the EDC data and the EMR data together in the user interface may be performed in any of the ways described herein, including by using mappings between EDC data and EMR data At operation 1508, the clinical research platform receives user input via the user interface. For example, in association with the display of the EDC data and the EMR data, a user may use the EMR data to review EDC data and the collection of the EDC data at a clinical research site and provide input representing findings from the review. The user may perform the review and provide the feedback while offsite from the clinical research site. The user input may represent an update to be made to EDC data, such as by annotating the EDC data with data representative of the user's findings.

At operation 1510, the clinical research platform sends an EDC data update to the first data store. The EDC data in the first data store is updated with the EDC data update to annotate the EDC data with the review feedback from the user.

Figure 16:
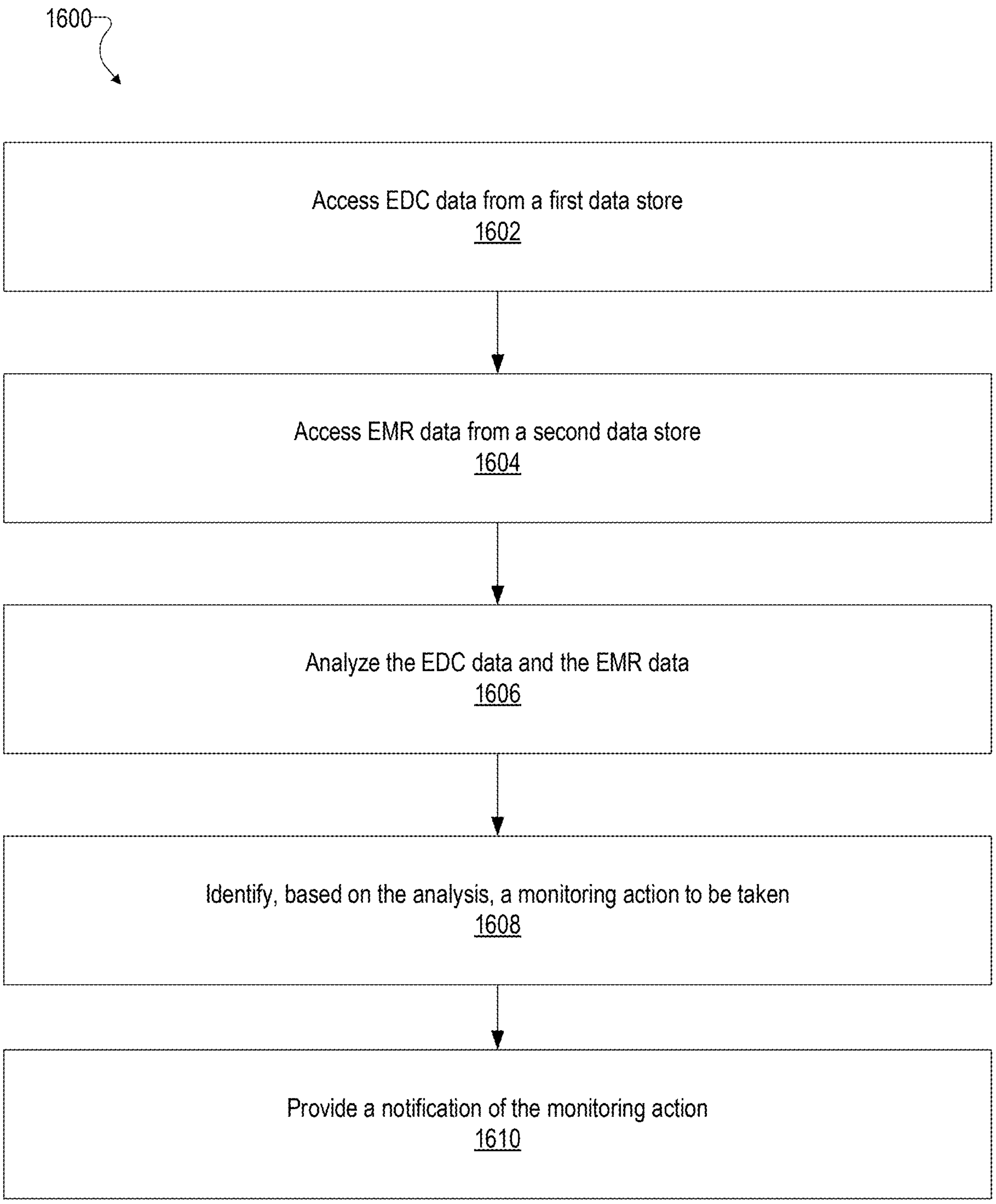
FIG. 16 illustrates an example method for remote management of clinical research.

FIG. 16 shows an illustrative method 1600 of remote management of clinical research. Any of the computing systems described herein may perform method 1600. For example, method 1600 may be performed by a clinical research platform such as CRP 1302. While FIG. 16 shows illustrative operations of method 1600, one or more operations may be combined, reordered, omitted, or added in other embodiments. The operations may be performed in any of the ways described herein.

At operation 1602, a clinical research platform accesses EDC data from a first data store.

At operation 1604, the clinical research platform accesses EMR data from a second data store.

At operation 1606, the clinical research platform analyzes the EDC data and the EMR data. The platform may be configured to analyze the EDC data and the EMR data in any suitable way that uses the EMR data to identify potential issues with the EDC data, such as non-compliance and/or protocol deviation in the collection of the data.

At operation 1608, the clinical research platform identifies, based on the analysis, a monitoring action to be taken. The monitoring action may be any action that may be performed by the platform or a user of the platform. The monitoring action may include, for example, a recommended action, a recommendation to check specific EDC data and/or EMR data for a potential issue related to data discrepancies, protocol deviations, adverse events, missing data, etc.

At operation 1610, the clinical research platform provides a notification of the monitoring action. The notification may be provided in any of the ways described herein.

In some embodiments, one or more trained artificial intelligence (AI) (e.g., machine learning (ML)) models may be used in the performance of one or more of the operations described herein. The model(s) may be trained using any suitable training technologies and datasets, including historical clinical research data (e.g., historical EDC data and related EMR data). The model(s) may be implemented using any suitable types of AI/ML models, including natural language processing (NLP) models, large language models (LLMs) agentic models, tiered models or other configurations of models, convolutions networks, etc. One or more of the trained models may be trained and/or tailored to the medical domain, such as by training the models on specific medical data. One or more others of the models may be generally trained models, such as sophisticated general large language models (LLMs), that are used with appropriate prompt engineering.

In some examples, one or more trained AI models may be configured to be used to identify EMR data that is related to CDR data such as clinical research patient data and/or EDC data. For example, IDP system 240 may be configured to use one or more trained AI models to identify such relationships and generate mappings between CDR data and EMR data. To this end, IDP system 240 may provide CDR data and EMR data as input to one or more trained AI models and use outputs from the one or more trained AI models to identify the relationships and generate mappings between CDR data and EMR data. This may identify more instances of EMR data as relevant to CDR data using indirect indicators of relationships between the data.

In some examples, one or more trained AI models may be configured to be used to analyze EDC data and related EMR data to identify potential issues with the data, the collection of the data, and/or remedial measures such as specific monitoring activities to be performed. SDM system 230 and/or IDP system 240 may be configured to provide the EDC data and related EMR data as input to one or more trained AI models and use outputs from the one or more trained AI models to identify potential issues with the data, the collection of the data, and/or remedial measures. SDM system 230 and/or IDP system 240 may be configured to surface the identified issues or measures, such as by annotating data with indicators of the identified issues or measures, generating and providing notifications (e.g., alerts) indicating the identified issues or measures, prioritizing in a monitoring workflow, review of the identified issues or measures over review of other data, etc. One or more trained AI models may be used to identify potential errors, deviations, and/or actions to be taken, perform automated monitoring of EMR source data sets, and perform analysis and interpretation of unstructured data with relevant associated monitoring actions to be taken. AI-model-based analysis and surfacing of identified issues or measures can help make review of EDC data in view of EMR data more efficient, more accurate, and less costly. For example, one or more trained AI models may be used to compare vital signs data in EDC data and EMR data and flag any discrepancies.

In some examples, one or more trained AI models may be configured to be used to analyze EMR data and flag specific instances of the EMR data that are identified as raising medical concerns.

The methods, systems, apparatuses, and products for remote management (e.g., remote monitoring) of clinical research source data and/or clinical research sites described herein can enable efficient, remote, offsite monitoring of clinical research data and sites. The remote monitoring can reduce travel and administrative burden of clinical research monitors (e.g., CRAs) for location monitoring visits and can increase monitoring productivity by surfacing EMR data in the context of EDC data that is to be verified and reviewed by the monitors. This can create the potential for remote monitoring anytime and from any location for the monitor, enabling the opportunity for more real-time oversight.

The methods, systems, apparatuses, and products increase productivity of the monitors by reducing the time traveling to multiple sites and reducing the time it takes to search for source data. In addition, standardized, near real-time remote access and oversight of clinical research data increases process compliance and reduces data incongruencies. In addition, remote visits by monitors can be standardized and increased in frequency due to the increased productivity and efficiency, which can lead to higher success rates of clinical studies and other health care related initiatives that require oversight and monitoring.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A computer-system-implemented method for remote management of clinical research using a multi-tenant clinical research platform, the method comprising:

granting a user having proper credentials access to the platform through a login process to manage one or more clinical study visits to one or more clinical research sites, the platform configured to access, via a first network connection, an electronic data capture (EDC) data store containing EDC data for a plurality of digitized clinical studies each having a set of clinical study protocols, the platform further configured to access, via a second network connection, an electronic medical record (EMR) data store containing EMR data about a plurality of patients, where the EMR data store and the EDC data store are separate from one another and implement different data specifications, the platform further configured to access and use mappings between EDC data for the one or more clinical study visits and EMR data associated with the one or more clinical study visits;

receiving, via a user interface, a request from the user to access a patient record for a patient's clinical study visit to a clinical research site;

retrieving and using, by the platform, the patient record to access EDC data for the patient's clinical study visit to the clinical research site;

retrieving, by the platform and based on the mappings, EMR data associated with the patient's clinical study visit to the clinical research site;

displaying, together via the user interface, the EDC data for the patient's clinical study visit to the clinical research site and the EMR data associated with the patient's clinical study visit to the clinical research site;

providing, via the user interface and in association with the displayed EDC data and EMR data, a review tool as part of a clinical research review workflow;

receiving user input via the review tool;

annotating, based on the user input, the EDC data for the patient's clinical study visit.

2. The computer-system-implemented method of claim 1, wherein retrieving the EMR data associated with the patient's clinical study visit to the clinical research site comprises selecting and requesting the EMR data based on a context of the EDC data.

3. The computer-system-implemented method of claim 1, wherein the EMR data store is implemented by an integrated data platform system configured to ingest raw EMR data from an EMR system of the clinical research site, transform the raw EMR data into United States Core Data for Interoperability (USCDI) format, and provide an interface through which the EMR data in USCDI format is accessible by the platform.

4. The computer-system-implemented method of claim 3, wherein the integrated data platform system is further configured to generate the mappings between the EDC data for the one or more clinical study visits and the EMR data associated with the one or more clinical study visits.

5. The computer-system-implemented method of claim 1, wherein the mappings comprise a mapping of a patient identifier for a patient represented in the EDC data to an EMR identifier for the patient represented in the EDC data.

6. The computer-system-implemented method of claim 1, wherein the mappings comprise a mapping of a clinical-study-protocol-defined data field represented in the EDC data to EDC data determined to be related to the data field.

7. The computer-system-implemented method of claim 1, wherein the mappings comprise a mapping of EDC data associated with a question in a clinical review workflow to EMR data determined to be related to the question.

8. The computer-system-implemented method of claim 1, wherein the platform is configured to prevent persistence of the EMR data retrieved by platform.

9. The computer-system-implemented method of claim 1, wherein the review tool comprises a user-selectable option to indicate a protocol deviation for the EDC data for the patient's clinical study visit to the clinical research site, based on a review of the EMR data associated with the patient's clinical study visit to the clinical research site.

10. The computer-system-implemented method of claim 1, wherein the review tool comprises a user-selectable option to indicate a verification of the EDC data for the patient's clinical study visit to the clinical research site, based on a review of the EMR data associated with the patient's clinical study visit to the clinical research site.

11. The computer-system-implemented method of claim 1, wherein the review tool comprises a user-selectable option to indicate non-compliance of the clinical review site for the EDC data for the patient's clinical study visit to the clinical research site, based on a review of the EMR data associated with the patient's clinical study visit to the clinical research site.

12. The computer-system-implemented method of claim 1, further comprising:

providing, by the platform, a notification of a protocol deviation by way of the user interface, the protocol deviation identified by the platform analyzing the EDC data and the EMR data.

13. The computer-system-implemented method of claim 1, further comprising:

providing, by the platform by way of the user interface, a notification of a monitoring action to be taken, the monitoring action identified by the platform analyzing the EDC data and the EMR data.

14. The computer-system-implemented method of claim 13, wherein a trained artificial intelligence model is used to analyze the EDC data and the EMR data and identify the monitoring action to be taken.

15. A multi-tenant clinical research platform system for remote management of clinical research sites, the system comprising:

an integrated data platform system comprising at least a first processor and a first non-transitory computer-readable memory storing first instructions executable by the first processor to:

access patient data from a clinical data repository;

ingest, from one or more clinical research sites, electronic medical record (EMR) data associated with patients identified by the patient data;

generate and store mappings between the patient data and the EMR data;

provide an egress interface through which the EMR data is externally accessible;

a source data management system communicatively coupled to the integrated data platform system by a secure network communication link and comprising at least a second processor and a second non-transitory computer-readable memory storing second instructions executable by the second processor to:

grant a user having proper credentials access through a login process to manage one or more clinical study visits to the one or more clinical research sites;

access, from the clinical data repository, electronic data capture (EDC) data for a patient;

access, from the integrated data platform system, electronic medical record (EMR) data for the patient;

integrate the EDC data and the EMR data for the patient into a clinical research review workflow; and provide, via a user interface, the clinical research review workflow with the integrated EDC data and EMR data.

16. The multi-tenant clinical research platform system of claim 15, wherein source data management system is configured to prevent persistence of the EMR data by the source data management system.

17. The multi-tenant clinical research platform system of claim 15, wherein the integrated data platform system is configured to transform the ingested EMR data into United States Core Data for Interoperability (USCDI) format.

18. The multi-tenant clinical research platform system of claim 15, wherein the mappings comprise a mapping of a patient identifier for a patient represented in the EDC data to an EMR identifier for the patient represented in the EDC data.

19. The multi-tenant clinical research platform system of claim 15, wherein the second instructions are further executable by the second processor to:

provide, via the user interface and in association with the integrated EDC data and EMR data, a review tool as part of the clinical research review workflow;

receive user input via the review tool;

annotate, based on the user input, the EDC data for the patient.

20. A computer program product embodied in a non-transitory computer readable storage medium and comprising computer instructions for:

granting a user having proper credentials access to a clinical research platform through a login process to manage one or more clinical study visits to one or more clinical research sites, the platform configured to access, via a first network connection, an electronic data capture (EDC) data store containing EDC data for a plurality of digitized clinical studies each having a set of clinical study protocols, the platform further configured to access, via a second network connection, an electronic medical record (EMR) data store containing EMR data about a plurality of patients, where the EMR data store and the EDC data store are separate from one another and implement different data specifications, the platform further configured to access and use mappings between EDC data for the one or more clinical study visits and EMR data associated with the one or more clinical study visits;

receiving, via a user interface, a request from the user to access a patient record for a patient's clinical study visit to a clinical research site;

retrieving and using, by the platform, the patient record to access EDC data for the patient's clinical study visit to the clinical research site;

retrieving, by the platform and based on the mappings, EMR data associated with the patient's clinical study visit to the clinical research site;

displaying, together via the user interface, the EDC data for the patient's clinical study visit to the clinical research site and the EMR data associated with the patient's clinical study visit to the clinical research site;

providing, via the user interface and in association with the displayed EDC data and EMR data, a review tool as part of a clinical research review workflow;

receiving user input via the review tool;

annotating, based on the user input, the EDC data for the patient's clinical study visit.

* * * * *